United States Patent
Moraitis

(10) Patent No.: US 11,213,526 B2
(45) Date of Patent: Jan. 4, 2022

(54) METHODS OF TREATING NEUROEPITHELIAL TUMORS USING SELECTIVE GLUCOCORTICOID RECEPTOR MODULATORS

(71) Applicant: Corcept Therapeutics, Inc., Menlo Park, CA (US)

(72) Inventor: Andreas G. Moraitis, Menlo Park, CA (US)

(73) Assignee: Corcept Therapeutics, Inc., Menlo Park, CA (US)

( * ) Notice: Subject to any disclaimer, the term of this patent is extended or adjusted under 35 U.S.C. 154(b) by 61 days.

(21) Appl. No.: 16/620,832

(22) PCT Filed: Jun. 18, 2018

(86) PCT No.: PCT/US2018/038075
§ 371 (c)(1),
(2) Date: Dec. 9, 2019

(87) PCT Pub. No.: WO2018/236749
PCT Pub. Date: Dec. 27, 2018

(65) Prior Publication Data
US 2020/0147082 A1 May 14, 2020

Related U.S. Application Data

(60) Provisional application No. 62/522,489, filed on Jun. 20, 2017.

(51) Int. Cl.
*A61K 31/4745* (2006.01)
*A61K 31/513* (2006.01)
*A61P 35/00* (2006.01)
*A61K 31/437* (2006.01)

(52) U.S. Cl.
CPC .......... *A61K 31/513* (2013.01); *A61K 31/437* (2013.01); *A61P 35/00* (2018.01)

(58) Field of Classification Search
CPC .... A61K 31/4745; A61K 31/513; A61P 35/00
USPC ................................................ 514/293, 274
See application file for complete search history.

(56) References Cited

U.S. PATENT DOCUMENTS

2013/0177559 A1 7/2013 Seehra et al.
2014/0030233 A1 1/2014 Altschul et al.

FOREIGN PATENT DOCUMENTS

WO 2013177559 A2 11/2013
WO 2015077530 A1 5/2015
WO 2016140867 A1 9/2016
WO WO 2017-151613 A1 * 9/2017 .......... C07D 471/04

OTHER PUBLICATIONS

Kach et al., "Selective Glucocorticoid Receptor Modulators (SGRMs) Delay Castrate-Resistant Prostate Cancer Growth", Molecular Cancer Therapeutics, vol. 16, No. 8, Aug. 2017, pp. 1680-1692.
Stringer-Reasor et al., "Glucocorticoid Receptor Activation Inhibits Chemotherapy-Induced Cell Death in High-Grade Serous Ovarian Carcinoma", Gynecol Oncol, vol. 138, Sep. 2015, pp. 656-662.
West et al., "Abstract PD3-02: Second-Generation Selective Glucocorticoid Receptor Modulators in Triple-Negative Breast Cancer", Cancer Research, vol. 76, No. 4, 2016, 2 pages.
PCT/US2018/038075, "International Search Report and Written Opinion", dated Dec. 20, 2018, 11 pages.
Lamberts et al., "Mifepristone (RU 486) Treatment of Meningiomas", Journal of Neurology, Neurosurgery & Psychiatry, vol. 55, No. 6, Jun. 1, 1992, pp. 486-490.
EP18821665.9, "Extended European Search Report", dated Jan. 22, 2021, 8 pages.

* cited by examiner

*Primary Examiner* — Charanjit Aulakh
(74) *Attorney, Agent, or Firm* — Kilpatrick Townsend & Stockton LLP

(57) ABSTRACT

Applicant discloses methods for treating a glucocorticoid receptor positive (GR$^+$) neuroepithelial tumor in a subject, comprising administering a selective glucocorticoid receptor modulator (SGRM) in an amount effective to reduce the tumor load in a subject. The GR$^+$ neuroepithelial tumor may be a neurofibromatosis type 2 (NF 2) tumor; the GR$^+$ neuroepithelial tumor may be a schwannoma, meningioma, or ependymoma. In embodiments, the GR$^+$ neuroepithelial tumor is not an adrenocorticotropic hormone (ACTH)-secreting tumor. In embodiments, the SGRM comprises a steroidal backbone. In embodiments, the SGRM is mifepristone. In embodiments, the SGRM comprises a non-steroidal backbone, such as, e.g., a cyclohexyl pyrimidine, a fused azadecalin, a heteroaryl ketone fused azadecalin, or an octahydro fused azadecalin backbone. The SGRM may be administered orally. The SGRM may be administered alone. In embodiments, the SGRM is administered with at least one non-SGRM therapy, e.g., a chemotherapy, a radiation therapy, or other therapeutic agents.

34 Claims, No Drawings

METHODS OF TREATING NEUROEPITHELIAL TUMORS USING SELECTIVE GLUCOCORTICOID RECEPTOR MODULATORS

BACKGROUND

Meningioma, schwannoma and ependymoma are neuroepithelial tumors frequently seen in patients with neurofibromatosis type 2 ("NF 2"). Meningioma accounts for about 36.1% of all primary brain tumors. Meningioma arises from meninges, the three thin layers of tissue covering the brain and spinal cord, and are often found near the top and the outer curve of the brain and at the base of the skull. Schwannoma accounts for about 8% of all primary brain tumors. Schwannoma is a nerve sheath tumor composed of Schwann cells. The tumor cells always stay on the outside of the nerve, but the tumor itself may either push the nerve aside and/or up against a bony structure. Both the incidence of meningioma and that of schwannoma increases with age and occur about twice as often in women as in men. Ependymoma accounts for about 5% of adult intracranial gliomas and up to 10% of childhood tumors of the central nervous system (CNS). Ependymomas develop from cells that line both the hollow cavities of the brain and the canal containing the spinal cord, but they usually arise from the floor of the fourth ventricle, situated in the lower back portion of the brain.

Conventional treatment options for neuroepithelial tumors such as meningioma, schwannoma, and ependymoma include surgery, radiation therapy, and chemotherapy. Surgery is currently the primary treatment option for patients having meningioma, schwannoma, or ependymoma. However, surgery often cannot completely remove tumors and may not be possible if the tumor has spread or it cannot be removed without damaging the brain. Radiation therapy and chemotherapy, taking advantage of the fact that cancer cells in general have higher proliferative capacity and are more sensitive to DNA damage, kills tumor cells by inflicting a generalized damage to DNA and destabilization of chromosomal structure, which eventually leads to destruction of cancer cells. Non-limiting examples of radiation therapies include γ-rays and x-rays and non-limiting examples of chemotherapy agents include bleomycin, cis-platin, vinblastine, cyclophosphamide, 5'-fluorouracil, and methotrexate. These treatments are particularly effective for those types of cancers that have defects in cell cycle checkpoint, which limits the ability of these cells to repair damaged DNA before undergoing cell division. The non-selective nature of these treatments, however, often results in severe and debilitating side effects. The systemic use of these drugs may result in damage to normally healthy organs and tissues and compromise the long-term health of the patient. Thus, there is a need for novel therapeutic options for treating neuroepithelial tumors, such as, e.g., meningioma, schwannoma, and ependymoma, and the present methods disclosed below meet these and other needs.

SUMMARY

Disclosed herein are methods for treating a GR$^+$ neuroepithelial tumor in a subject (where "GR$^+$" means that the tumor expresses the glucocorticoid receptor (GR)), the methods comprising administering to the subject a glucocorticoid receptor modulator (GRM), such as a selective glucocorticoid receptor modulator (SGRM), in an amount effective to reduce the tumor load of the GR$^+$ neuroepithelial tumor in the subject with the proviso that the subject not be otherwise suffering from a disorder treatable with a SGRM. Non-limiting examples of disorders where treatment comprising administering SGRMs are indicated as beneficial include Cushing's syndrome, psychiatric disorders such as psychotic major depression, cocaine addition, stress disorders, postpartum psychosis, and cancers treatable with combinations of taxanes and SGRMs (e.g., breast and prostate). In embodiments of the methods disclosed herein, the GR$^+$ neuroepithelial tumor is not an adrenocorticotropic hormone (ACTH)-secreting tumor. In some embodiments, the GR$^+$ neuroepithelial tumor is neurofibromatosis type 2 (NF 2). In some embodiments, the GR$^+$ neuroepithelial tumor is a tumor selected from schwannoma, meningioma, and ependymoma.

In some cases, the SGRM is orally administered. In some cases, the SGRM is administered by transdermal application, by a nebulized suspension, or by an aerosol spray. In some cases, the SGRM is a nonsteroidal glucocorticoid receptor modulator. In some cases, the nonsteroidal glucocorticoid receptor modulator is orally administered. In some cases, the nonsteroidal glucocorticoid receptor modulator is administered by transdermal application, by a nebulized suspension, or by an aerosol spray. In some cases, the SGRM is administered to the subject for at least two weeks. In some cases, the SGRM is administered to the subject for at least three weeks, or four weeks, or two months, or three months, or longer.

In some cases, the effective amount of the SGRM is a daily dose of between 1 and 100 mg/kg/day, wherein the SGRM is administered alone or with at least one non-SGRM therapy, e.g., a chemotherapy, a radiation therapy, or other therapeutic agents. In some embodiments, the daily dose is 1, 2, 4, 6, 8, 10, 12, 14, 16, 18, 20, 30, 40, 50 60, 70, 80, 90 or 100 mg/kg/day. In some cases, the nonsteroidal glucocorticoid receptor modulator is administrated for at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, or 80 weeks.

In some embodiments, the glucocorticoid receptor modulator, such as a SGRM, comprises a steroidal backbone with at least one phenyl-containing moiety in the 11-β position of the steroidal backbone. In some cases, the phenyl-containing moiety in the 11-β position of the steroidal backbone is a dimethylaminophenyl moiety. In some cases, the glucocorticoid receptor modulator is mifepristone. In some embodiments, the glucocorticoid receptor modulator is selected from the group consisting of 11β-(4-dimethylaminoethoxyphenyl)-17α-propynyl-17β-hydroxy-4,9 estradien-3-one and (17α)-17-hydroxy-19-(4-methylphenyl)androsta-4,9 (11)-dien-3-one. In some embodiments, the glucocorticoid receptor modulator is (11β,17β)-11-(1,3-benzodioxol-5-yl)-17-hydroxy-17-(1-propynyl)estra-4,9-dien-3-one.

In some embodiments, the glucocorticoid receptor modulator, such as a SGRM, has a non-steroidal backbone. In some cases, the glucocorticoid receptor modulator backbone is a cyclohexyl pyrimidine. In some cases, wherein the cyclohexyl pyrimidine has the following formula:

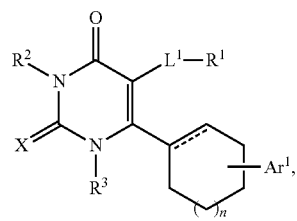

wherein the dashed line is absent or a bond; X is selected from the group consisting of O and S; $R^1$ is selected from the group consisting of cycloalkyl, heterocycloalkyl, aryl and heteroaryl, optionally substituted with from 1 to 3 $R^{1a}$ groups; each $R^{1a}$ is independently selected from the group consisting of H, $C_{1-6}$ alkyl, $C_{2-6}$ alkenyl, $C_{2-6}$ alkynyl, $C_{1-6}$ alkoxy, $C_{1-6}$ alkyl $OR^{1b}$, halogen, $C_{1-6}$ haloalkyl, $C_{1-6}$ haloaloxy, $OR^{1b}$, $NR^{1b}R^{1c}$, $C(O)R^{1b}$, $C(O)OR^{1b}$, $OC(O)R^{1b}$, $C(O)NR^{1b}R^{1c}$, $NR^{1b}C(O)R^{1c}$, $SO_2R^{1b}$, $SO_2NR^{1b}R^{1c}$, cycloalkyl, heterocycloalkyl, aryl and heteroaryl; $R^{1b}$ and $R^{1c}$ are each independently selected from the group consisting of H and $C_{1-6}$ alkyl; $R^2$ is selected from the group consisting of H, $C_{1-6}$ alkyl, $C_{1-6}$ alkyl-$OR^{1b}$, $C_{1-6}$ alkyl $NR^{1b}R^{1c}$ and $C_{1-6}$ alkylene heterocycloalkyl; $R^3$ is selected from the group consisting of H and $C_{1-6}$ alkyl; Ar is aryl, optionally substituted with 1-4 $R^4$ groups; each $R^4$ is independently selected from the group consisting of H, $C_{1-6}$ alkyl, $C_{1-6}$ alkoxy, halogen, $C_{1-6}$ haloalkyl and $C_{1-6}$ haloalkoxy; $L^1$ is a bond or $C_{1-6}$ alkylene; and subscript n is an integer from 0 to 3, or salts and isomers thereof.

In some cases, the glucocorticoid receptor modulator backbone is a fused azadecalin. In some cases, the fused azadecalin is a compound having the following formula:

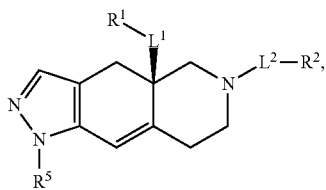

wherein $L^1$ and $L^2$ are members independently selected from a bond and unsubstituted alkylene; $R^1$ is a member selected from unsubstituted alkyl, unsubstituted heteroalkyl, unsubstituted heterocycloalkyl, $-OR^{1A}$, $NR^{1C}R^{1D}$, $-C(O)NR^{1C}R^{1D}$, and $-C(O)OR^{1A}$, wherein $R^{1A}$ is a member selected from hydrogen, unsubstituted alkyl and unsubstituted heteroalkyl, $R^{1C}$ and $R^{1D}$ are members independently selected from unsubstituted alkyl and unsubstituted heteroalkyl, wherein $R^{1C}$ and $R^{1D}$ are optionally joined to form an unsubstituted ring with the nitrogen to which they are attached, wherein said ring optionally comprises an additional ring nitrogen; $R^2$ has the formula:

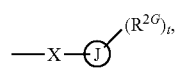

wherein $R^{2G}$ is a member selected from hydrogen, halogen, unsubstituted alkyl, unsubstituted heteroalkyl, unsubstituted cycloalkyl, unsubstituted heterocycloalkyl, $-CN$, and $-CF_3$; J is phenyl; t is an integer from 0 to 5; X is $-S(O_2)-$; and $R^5$ is phenyl optionally substituted with 1-5 $R^{5A}$ groups, wherein $R^{5A}$ is a member selected from hydrogen, halogen, $-OR^{5A1}$, $S(O_2)NR^{5A2}R^{5A3}$, $-CN$, and unsubstituted alkyl, wherein $R^{5A1}$ is a member selected from hydrogen and unsubstituted alkyl, and $R^{5A2}$ and $R^{5A3}$ are members independently selected from hydrogen and unsubstituted alkyl, or salts and isomers thereof.

In some cases, the glucocorticoid receptor modulator backbone is a heteroaryl ketone fused azadecalin or an octahydro fused azadecalin. In some cases, the heteroaryl ketone fused azadecalin has the formula:

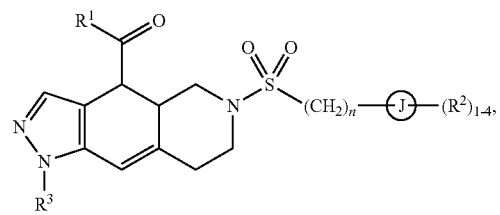

wherein $R^1$ is a heteroaryl ring having from 5 to 6 ring members and from 1 to 4 heteroatoms each independently selected from the group consisting of N, O and S, optionally substituted with 1-4 groups each independently selected from $R^{1a}$; each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, CN, N-oxide, $C_{3-8}$ cycloalkyl, and $C_{3-8}$ heterocycloalkyl; ring J is selected from the group consisting of a cycloalkyl ring, a heterocycloalkyl ring, an aryl ring and a heteroaryl ring, wherein the heterocycloalkyl and heteroaryl rings have from 5 to 6 ring members and from 1 to 4 heteroatoms each independently selected from the group consisting of N, O and S; each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, CN, OH, $NR^{2a}R^{2b}$, $C(O)R^{2a}$, $C(O)OR^{2a}$, $C(O)NR^{2a}R^{2b}$, $SR^{2a}$, $S(O)R^{2a}$, $S(O)_2R^{2a}$, $C_{3-8}$ cycloalkyl, and $C_{3-8}$ heterocycloalkyl, wherein the heterocycloalkyl groups are optionally substituted with 1-4 $R^{2c}$ groups; alternatively, two $R^2$ groups linked to the same carbon are combined to form an oxo group ($=O$); alternatively, two $R^2$ groups are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2d}$ groups; $R^{2a}$ and $R^{2b}$ are each independently selected from the group consisting of hydrogen and $C_{1-6}$ alkyl; each $R^{2c}$ is independently selected from the group consisting of hydrogen, halogen, hydroxy, $C_{1-6}$ alkoxy, $C_{1-6}$ haloalkoxy, CN, and $NR^{2a}R^{2b}$; each $R^{2d}$ is independently selected from the group consisting of hydrogen and $C_{1-6}$ alkyl, or two $R^{2d}$ groups attached to the same ring atom are combined to form ($=O$); $R^3$ is selected from the group consisting of phenyl and pyridyl, each optionally substituted with 1-4 $R^{3a}$ groups; each $R^{3a}$ is independently selected from the group consisting of hydrogen, halogen, and $C_{1-6}$ haloalkyl; and subscript n is an integer from 0 to 3; or salts and isomers thereof.

In some cases, the octahydro fused azadecalin has the formula:

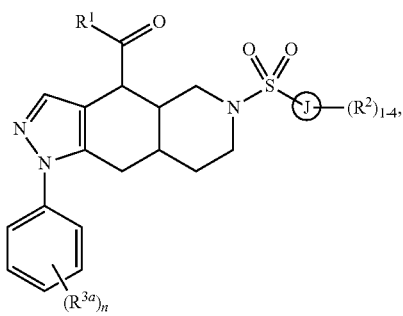

wherein $R^1$ is a heteroaryl ring having from 5 to 6 ring members and from 1 to 4 heteroatoms each independently selected from the group consisting of N, O and S, optionally substituted with 1-4 groups each independently selected from $R^{1a}$; each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, N-oxide, and $C_{3-8}$ cycloalkyl; ring J is selected from the group consisting of an aryl ring and a heteroaryl ring having from 5 to 6 ring members and from 1 to 4 heteroatoms each independently selected from the group consisting of N, O and S; each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, CN, OH, $NR^{2a}R^{2b}$, $C(O)R^{2a}$, $C(O)OR^{2a}$, $C(O)NR^{2a}R^{2b}$, $SR^{2a}$, $S(O)R^{2a}$, $S(O)_2R^{2a}$, $C_{3-8}$ cycloalkyl, and $C_{3-8}$ heterocycloalkyl having from 1 to 3 heteroatoms each independently selected from the group consisting of N, O and S; alternatively, two $R^2$ groups on adjacent ring atoms are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2c}$ groups; $R^{2a}$, $R^{2b}$ and $R^{2c}$ are each independently selected from the group consisting of hydrogen and $C_{1-6}$ alkyl; each $R^{3a}$ is independently halogen; and subscript n is an integer from 0 to 3, or salts and isomers thereof.

In some cases, the SGRM is CORT125134, i.e., (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone, which has the following structure:

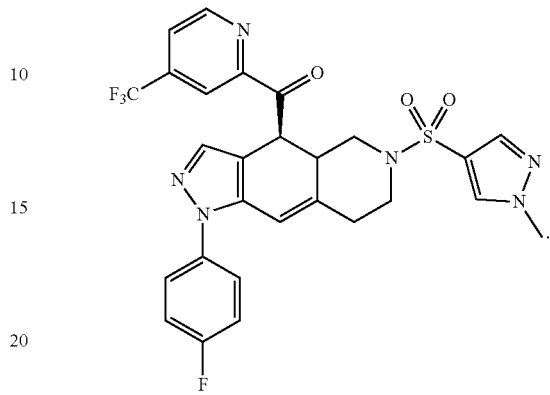

In some cases, the SGRM is CORT125281, i.e., ((4aR,8aS)-1-(4-fluorophenyl)-6-((2-methyl-2H-1,2,3-triazol-4-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone, which has the following structure:

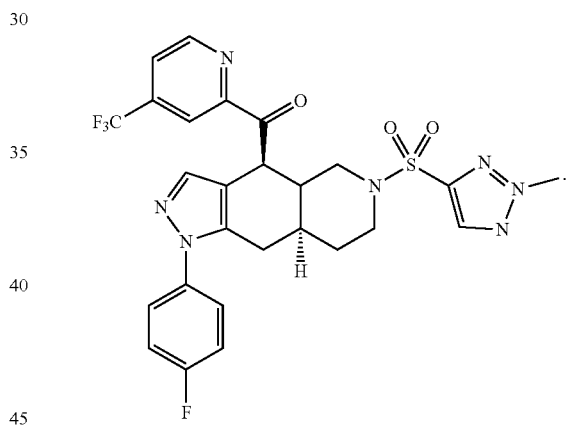

DETAILED DESCRIPTION

A. Introduction

This method disclosed herein can be used to treat a patient hosting a neuroepithelial tumors such as, e.g., a meningioma, a schwannoma, or an ependymoma, by administering at an effective amount of SGRM alone or in combination with other therapies.

B. Definitions

As used herein, the term "subject" or "patient" refers to a human or non-human organism. Thus, the methods and compositions described herein are applicable to both human and veterinary disease. In certain embodiments, subjects are "patients," i.e., living humans that are receiving medical care for a disease or condition. This includes persons with no defined illness who are being investigated for signs of pathology. Preferred are subjects who have an existing diagnosis of a particular cancer which is being targeted by the compositions and methods disclosed herein. In some cases, a subject may suffer from one or more types of cancer simultaneously, at least one of which is targeted by the compositions and methods disclosed herein. Preferred cancers for treatment with the compositions described herein include, but are not limited to neuroepithelial tumors, such as meningioma, schwannoma, and ependymoma.

As used herein, the term "tumor load" or "tumor burden" generally refers to the number of cancer cells, the size of a tumor, or the amount of cancer in the body in a subject at any given time. Tumor load can be detected by e.g., measuring the expression of tumor specific genetic markers and measuring tumor size by a number of well-known, biochemical or imaging methods disclosed herein, infra.

As used herein, the term "effective amount" or "therapeutic amount" refers to an amount of a pharmacological agent effective to treat, eliminate, or mitigate at least one symptom of the disease being treated. In some cases, "therapeutically effective amount" or "effective amount" can refer to an amount of a functional agent or of a pharmaceutical composition useful for exhibiting a detectable therapeutic or inhibitory effect. The effect can be detected by any assay method known in the art. The effective amount can be an amount effective to invoke an antitumor response. The effective amount can be an amount effective to evoke a humoral and/or cellular immune response in the recipient subject leading to growth inhibition or death of target cells. For the purpose of this disclosure, the therapeutic amount of SGRM is an amount that would reduce tumor load or bring about other desired beneficial clinical outcomes related to cancer improvement when used alone or with other therapies.

As used herein, the terms "administer," "administering," "administered" or "administration" refer to providing a compound or a composition (e.g., one described herein), to a subject or patient.

As used herein, the term "compound" is used to denote a molecular moiety of unique, identifiable chemical structure. A molecular moiety ("compound") may exist in a free species form, in which it is not associated with other molecules. A compound may also exist as part of a larger aggregate, in which it is associated with other molecule(s), but nevertheless retains its chemical identity. A solvate, in which the molecular moiety of defined chemical structure ("compound") is associated with a molecule(s) of a solvent, is an example of such an associated form. A hydrate is a solvate in which the associated solvent is water. The recitation of a "compound" refers to the molecular moiety itself (of the recited structure), regardless whether it exists in a free form or an associated form.

As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

As used herein, the term "mineralocorticoid receptor" (MR) refers to type I glucocorticoid receptor, that binds mineralocorticoids. The MR binds aldosterone, and is also referred to as the "aldosterone receptor".

As used herein, the term "Glucocorticoid receptor" ("GR") refers to the type II glucocorticoid receptor ("type II" of the family of intracellular receptors which specifically bind to cortisol and/or cortisol analogs such as dexamethasone (See, e.g., Turner & Muller, J. Mol. Endocrinol. Oct. 1, 2005 35 283-292)). The GR is also referred to as the cortisol receptor. The term GR includes isoforms of GR, recombinant GR and mutated GR. A cell, tissue, organ, tumor, or other animal portion or material that expresses GR is termed GR "positive" (GR$^+$).

The term "Glucocorticoid receptor modulator" and its acronym "GRM", also known and described in the scientific and patent literature as, e.g., either a glucocorticoid receptor agonist or a glucocorticoid receptor antagonist, refers to any compound which alters, e.g., inhibits any biological response associated with the binding of GR to an agonist. For example, a GR agonist, such as dexamethasone, increases the activity of tyrosine aminotransferase (TAT) in HepG2 cells (a human liver hepatocellular carcinoma cell line; ECACC, UK). Accordingly, GRMs as discussed herein can be identified by measuring the ability of the compound to inhibit the effect of dexamethasone. TAT activity can be measured as outlined in the literature by A. Ali et al., J. Med. Chem., 2004, 47, 2441-2452. A modulator is a compound with an $IC_{50}$ (half maximal inhibition concentration) of less than 10 micromolar. See Example 1, infra.

As used herein, the term "selective glucocorticoid receptor modulator" and its acronym "SGRM" refer to any composition or compound which alters, e.g., inhibits any biological response associated with the binding of a GR to an agonist. By "selective," the drug preferentially binds to the GR rather than other nuclear receptors, such as the progesterone receptor (PR), the mineralocorticoid receptor (MR) or the androgen receptor (AR). It is preferred that the selective glucocorticoid receptor modulator bind GR with an affinity that is 10× greater ($\frac{1}{10}^{th}$ the $K_d$ value) than its affinity to the MR, AR, or PR, both the MR and PR, both the MR and AR, both the AR and PR, or to the MR, AR, and PR. In a more preferred embodiment, the selective glucocorticoid receptor modulator (SGRM) binds GR with an affinity that is 100× greater ($\frac{1}{100}^{th}$ the $K_d$ value) than its affinity to the MR, AR, or PR, both the MR and PR, both the MR and AR, both the AR and PR, or to the MR, AR, and PR. In another embodiment, the selective glucocorticoid receptor modulator binds GR with an affinity that is 1000× greater ($\frac{1}{1000}^{th}$ the $K_d$ value) than its affinity to the MR, AR, or PR, both the MR and PR, both the MR and AR, both the AR and PR, or to the MR, AR, and PR.

As used herein, the terms "antiglucocorticoid" and "antiglucocorticoid activity" refer to compounds, and the actions of such compounds, which oppose, reduce, or prevent one or more of: the binding of glucocorticoid receptor ligands to GR, the activation of GR, the expression of GR, levels of glucocorticoid ligands, or otherwise modulate GR so as to reduce or abolish GR action or activity.

As used herein, the term "composition" is intended to encompass a product comprising the specified ingredients such as the said compounds, their tautomeric forms, their derivatives, their analogues, their stereoisomers, their polymorphs, their pharmaceutically acceptable salts, esters, ethers, metabolites, mixtures of isomers, their pharmaceutically acceptable solvates and pharmaceutically acceptable compositions in specified amounts, as well as any product which results, directly or indirectly, from combination of the specified ingredients in the specified amounts. Such term in relation to a pharmaceutical composition is intended to encompass a product comprising the active ingredient(s), and the inert ingredient(s) that make up the carrier, as well as any product which results, directly or indirectly, in combination, complexation or aggregation of any two or more of the ingredients, or from dissociation of one or more of the ingredients, or from other types of reactions or interactions of one or more of the ingredients. Accordingly, the pharmaceutical compositions disclosed herein are meant to encompass any composition made by admixing compounds discussed herein and their pharmaceutically acceptable carriers.

In some embodiments, the term "consisting essentially of" refers to a composition in a formulation whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" can refer to compositions which contain the active ingredient and components which facilitate the release of the active ingredient. For example, the composition can contain one or more components that provide extended release of the active ingredient over time to the subject. In some embodiments, the term "consisting" refers to a composition, which contains the active ingredient and a pharmaceutically acceptable carrier or excipient.

The term "steroidal backbone" in the context of glucocorticoid receptor antagonists containing such refers to glucocorticoid receptor antagonists that contain modifications of the basic structure of cortisol, an endogenous steroidal glucocorticoid receptor ligand. The basic structure of a steroidal backbone is provided as Formula I:

Formula I: Steroidal Backbone

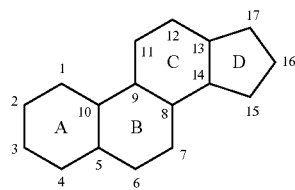

The two most commonly known classes of structural modifications of the cortisol steroid backbone to create glucocorticoid antagonists include modifications of the 11-β hydroxy group and modification of the 17-β side chain (See, e. g., Lefebvre (1989) J. Steroid Biochem. 33: 557-563).

As used herein, the phrase "non-steroidal backbone" in the context of SGRMs refers to SGRMs that do not share structural homology to, or are not modifications of, cortisol with its steroid backbone containing seventeen carbon atoms, bonded in four fused rings. Such compounds include synthetic mimetics and analogs of proteins, including partially peptidic, pseudopeptidic and non-peptidic molecular entities.

Non-steroidal GRMs, such as SGRM compounds, include GRMs having a fused azadecalin backbone, a heteroaryl ketone fused azadecalin backbone, and an octahydro fused azadecalin backbone. Exemplary GRMs having a fused azadecalin backbone include those described in U.S. Pat. Nos. 7,928,237 and 8,461,172. Exemplary SGRMs having a heteroaryl ketone fused azadecalin backbone include those described in U.S. 2014/0038926, now U.S. Pat. No. 8,859,774. Exemplary GRMs having an octohydro fused azadecalin backbone include those described in U.S. Patent Appl. Publication No. 2015/0148341, entitled Octahydro Fused Azadecalin Glucocorticoid Receptor Modulators.

Where substituent groups are specified by their conventional chemical formulae, written from left to right, they equally encompass the chemically identical substituents that would result from writing the structure from right to left, e.g., —CH$_2$O— is equivalent to —OCH$_2$—.

"Alkyl" refers to a straight or branched, saturated, aliphatic radical having the number of carbon atoms indicated. Alkyl can include any number of carbons, such as C$_{1-2}$, C$_{1-3}$, C$_{1-4}$, C$_{1-5}$, C$_{1-6}$, C$_{1-7}$, C$_{1-8}$, C$_{1-9}$, C$_{1-10}$, C$_{2-3}$, C$_{2-4}$, C$_{2-5}$, C$_{2-6}$, C$_{3-4}$, C$_{3-5}$, C$_{3-6}$, C$_{4-5}$, C$_{4-6}$, and C$_{5-6}$. For example, C$_{1-6}$ alkyl includes, but is not limited to, methyl, ethyl, propyl, isopropyl, butyl, isobutyl, sec.butyl, tert.butyl, pentyl, isopentyl, and hexyl.

"Alkoxy" refers to an alkyl group having an oxygen atom that connects the alkyl group to the point of attachment: alkyl-O—. As for the alkyl group, alkoxy groups can have any suitable number of carbon atoms, such as C$_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc.

"Halogen" refers to fluorine, chlorine, bromine, and iodine.

"Haloalkyl" refers to alkyl, as defined above, where some or all of the hydrogen atoms are replaced with halogen atoms. As for the alkyl group, haloalkyl groups can have any suitable number of carbon atoms, such as C$_{1-6}$, and include trifluoromethyl, fluoromethyl, etc.

The term "perfluoro" can be used to define a compound or radical where all the hydrogens are replaced with fluorine. For example, perfluoromethane includes 1,1,1-trifluoromethyl.

"Haloalkoxy" refers to an alkoxy group where some or all of the hydrogen atoms are substituted with halogen atoms. As for the alkyl group, haloalkoxy groups can have any suitable number of carbon atoms, such as C$_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2-trifluoroethoxy, and perfluoroethoxy.

"Cycloalkyl" refers to a saturated or partially unsaturated, monocyclic, fused bicyclic, or bridged polycyclic ring assembly containing from 3 to 12 ring atoms, or the number of atoms indicated. Cycloalkyl can include any number of carbons, such as C$_{3-6}$, C$_{4-6}$, C$_{5-6}$, C$_{3-8}$, C$_{4-8}$, C$_{5-8}$, C$_{6-8}$, C$_{3-9}$, C$_{3-10}$, C$_{3-11}$, and C$_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene, and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic C$_{3-8}$ cycloalkyl, exemplary groups include, but are not limited to, cyclopropyl, cyclobutyl, cyclopentyl, cyclohexyl, cycloheptyl, and cyclooctyl. When cycloalkyl is a saturated monocyclic C$_{3-6}$ cycloalkyl, exemplary groups include, but are not limited to, cyclopropyl, cyclobutyl, cyclopentyl, and cyclohexyl.

"Heterocycloalkyl" refers to a saturated ring system having from 3 to 12 ring members and from 1 to 4 heteroatoms of N, O, and S. Additional heteroatoms can also be useful, including but not limited to, B, Al, Si, and P. The heteroatoms can also be oxidized, such as, but not limited to, —S(O)— and —S(O)$_2$—. Heterocycloalkyl groups can include any number of ring atoms, such as 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxalidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Aryl" refers to an aromatic ring system having any suitable number of ring atoms and any suitable number of rings. Aryl groups can include any suitable number of ring atoms, such as 6, 7, 8, 9, 10, 11, 12, 13, 14, 15, or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, that has a methylene linking group. Some aryl groups have from 6 to 12 ring members, such as phenyl, naphthyl, or biphenyl. Other aryl groups have from 6 to 10 ring members, such as phenyl or naphthyl. Some other aryl groups have 6 ring members, such as phenyl. Aryl groups can be substituted or unsubstituted.

"Heteroaryl" refers to a monocyclic, fused bicyclic, or tricyclic aromatic ring assembly containing 5 to 16 ring atoms, where from 1 to 5 of the ring atoms are a heteroatom such as N, O, or S. Additional heteroatoms can also be useful, including but not limited to, B, Al, Si, and P. The heteroatoms can also be oxidized, such as, but not limited to, N-oxide, —S(O)—, and —S(O)$_2$—. Heteroaryl groups can include any number of ring atoms, such as 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5; or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4-, and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

The heteroaryl groups can be linked via any position on the ring. For example, pyrrole includes 1-, 2-, and 3-pyrrole; pyridine includes 2-, 3- and 4-pyridine; imidazole includes 1-, 2-, 4- and 5-imidazole; pyrazole includes 1-, 3-, 4- and 5-pyrazole; triazole includes 1-, 4- and 5-triazole; tetrazole includes 1- and 5-tetrazole; pyrimidine includes 2-, 4-, 5- and 6-pyrimidine; pyridazine includes 3- and 4-pyridazine; 1,2,3-triazine includes 4- and 5-triazine; 1,2,4-triazine includes 3-, 5- and 6-triazine; 1,3,5-triazine includes 2-triazine; thiophene includes 2- and 3-thiophene; furan includes 2- and 3-furan; thiazole includes 2-, 4- and 5-thiazole; isothiazole includes 3-, 4- and 5-isothiazole; oxazole includes 2-, 4- and 5-oxazole; isoxazole includes 3-, 4- and 5-isoxazole; indole includes 1-, 2- and 3-indole; isoindole includes 1- and 2-isoindole; quinoline includes 2-, 3- and 4-quinoline; isoquinoline includes 1-, 3- and 4-isoquinoline; quinazoline includes 2- and 4-quinazoline; cinnoline includes 3- and 4-cinnoline; benzothiophene includes 2- and 3-benzothiophene; and benzofuran includes 2- and 3-benzofuran.

Some heteroaryl groups include those having from 5 to 10 ring members and from 1 to 3 ring atoms including N, O, or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring heteroatoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

"Heteroatoms" refers to O, S, or N.

"Salt" refers to acid or base salts of the compounds used in the methods disclosed herein. Illustrative examples of pharmaceutically-acceptable salts are mineral acid (hydrochloric acid, hydrobromic acid, phosphoric acid, and the like) salts, organic acid (acetic acid, propionic acid, glutamic acid, citric acid, and the like) salts, and quaternary ammonium (methyl iodide, ethyl iodide, and the like) salts. It is understood that the pharmaceutically-acceptable salts are non-toxic. Additional information on suitable pharmaceutically-acceptable salts can be found in Remington's Pharmaceutical Sciences, 17th ed., Mack Publishing Company, Easton, Pa., 1985, which is incorporated herein by reference.

"Isomers" refers to compounds with the same chemical formula but which are structurally distinguishable.

"Tautomer" refers to one of two or more structural isomers which exist in equilibrium and which are readily converted from one form to another.

Descriptions of compounds discussed herein are limited by principles of chemical bonding known to those skilled in the art. Accordingly, where a group may be substituted by one or more of a number of substituents, such substitutions are selected so as to comply with principles of chemical bonding and to produce compounds which are not inherently unstable—and/or would be known to one of ordinary skill in the art as likely to be unstable under ambient conditions—such as aqueous, neutral, or physiological conditions.

"Pharmaceutically-acceptable excipient" and "pharmaceutically-acceptable carrier" refer to a substance that aids the administration of an active agent to—and absorption by—a subject and can be included in the compositions discussed herein without causing a significant adverse toxicological effect on the patient. Non-limiting examples of pharmaceutically-acceptable excipients include water, NaCl, normal saline solutions, lactated Ringer's, normal sucrose, normal glucose, binders, fillers, disintegrants, lubricants, coatings, sweeteners, flavors and colors, and the like. One of ordinary skill in the art will recognize that other pharmaceutical excipients are useful in compositions for use in the methods disclosed herein.

C. GR Positive (GR$^+$) Neuroepithelial Tumors

The methods disclosed herein are useful for treating a GR$^+$ neuroepithelial tumor by administering an effective amount of SGRM. Neuroepithelial tumors arise from cells that developmentally stem from primitive neuroepithelia and represent the largest group of intracranial neoplasms. See, e.g., the "Oncology Encyclopedia" article at the link "CNS-tumors/Diagnoses/Intracranial-tumors/Background/Histology" on the oncolex.org website entitled "Histology of Intracranial Tumors". Based on the premise that each type of tumor results from the abnormal growth of a specific cell type, neuroepithelial tumors can be categorized into the following classes according to the World Health Organization (WHO): astrocytic tumors, oligodendroglial tumors, ependymal cell tumors, mixed gliomas, neuroepithelial tumors of uncertain origin, tumors of the choroid plexus, neuronal and mixed neuronal-glial tumors, pineal parenchyma tumors, and tumors with neuroblastic or glioblastic elements (embryonal tumors).

GR expression status in these various neuroepithelial tumors are examined by using one or more of the routine biochemical analyses. In some embodiments, GR expression is determined by detecting GR transcript expression, using methods such as microarray and RT-PCR. In other embodiments, GR expression is determined by detecting protein expression, using methods such as, western blot analysis and immunohistochemistry staining. In yet other embodiments, the GR expression is determined using a combination of these methods.

In a preferred embodiment, immunohistochemistry staining is performed and a H-score method is used to quantify the expression of GR on tumor tissues. In one exemplar assay, Formalin-fixed, paraffin-embedded tumor tissue sections are deparaffinized and treated with antigen retrieval solution to render the glucocorticoid receptors readily accessible to anti-GR antibodies. Anti-GR antibodies are then incubated with the tissue sections and the antibodies bound to the GR on the tissue sections are detected by addition of a horse peroxidase (HRP) conjugated secondary antibody that recognizes the anti-GR antibody. The HRP on the secondary antibody conjugate catalyzes a colorimetric reaction and upon contacting the appropriate substrate, produces a staining in the locations where GR is present. In one approach, the intensity level of the GR staining is represented by 0 for negative staining, 1+ for weak staining, 2+ for moderate staining, and 3+ for strong staining, (see the article entitled "ihc scoring" available at www.ihcworld.com). The percentage of GR$^+$ cells of each intensity level is multiplied with the intensity level, and the results for all intensity levels are summed to generate a H-score between 0-300. In one embodiment, the tumor type having a H-score equal to or higher than a predetermined threshold is considered GR$^+$ tumor. In a preferred embodiment, the threshold is 150. In another embodiment, a GR$^+$ tumor is one that has at least 10% tumor cells showing GR staining at any intensity.

D. Diagnosing Meningioma, Schwannoma, and Ependymoma

Schwannoma, meningioma, and ependymoma are neuroepithelial tumors and are typically GR$^+$. These tumors are frequently observed in patients with Neurofibromatosis type 2 ("NF2", a.k.a. "MISME Syndrome", for "Multiple Inherited Schwannomas, Meningiomas, and Ependymomas"). NF2 is caused by mutations in the NF2 gene, which gives a person an increased risk of developing cancerous and benign tumors and other symptoms of NF2. The NF2 gene encodes a protein called merlin (also known as schwannomin). This protein is produced in the nervous system, particularly in Schwann cells, which surround and insulate nerve cells (neurons) in the brain and spinal cord. The merlin protein acts as a tumor suppressor and mutations in the NF2 gene lead to the production of a nonfunctional version of the merlin protein that cannot regulate the growth and division of cells.

Signs of NF2 usually develop in late teenage years or early 20s. NF2 patients have an increased risk of developing cataracts in the eyes and benign skin tumors and may have light brown pigmentation in their skin. Symptoms of NF2 often include hearing loss, tinnitus, dysequilibrium, headache, facial numbness and weakness. NF2 Patients may also exhibit abnormal corneal reflex, nystagmus, facial hypesthesia upon clinical examinations and show enlargement of the porus acousticus internus in the CT scan, enhancing tumours in the region of cerebello-pontine angle in gadolinium-enhanced MRI scans, hearing loss in audiometric studies and perhaps pathological findings in Electronystagmography. Genetic testing for mutations in the NF2 gene is available for patients diagnosed with NF2 to confirm the diagnosis.

Patients having meningioma may exhibit symptoms comprising one or more of the following: changes in vision, such as double vision or blurriness; hearing loss; memory loss; loss of smell; facial pain; headaches that worsen with time; personality changes; weakness in an arm or leg; and seizures. One or more of imaging based methods, such as, magnetic resonance imaging (MRI), computed tomography (CT), X-ray, cerebral angiogram, and positron emission tomography (PET) scan, or ultrasonography (US), are often performed on subjects suspected of having meningioma, e.g., based on exhibition of the related clinical symptoms. Results from these imaging tests are often combined with the patient's medical history, physical examination and neurological tests to provide accurate diagnosis as well as information regarding the origin of the meningioma and whether or where it has spread.

Common symptoms of schwannoma include, but are not limited to, one or more of the following: one-sided hearing loss and buzzing or ringing in the ear, dizziness, facial paralysis, difficulty in swallowing, impaired eye movement, taste disturbances, and unsteadiness, altered facial and corneal sensation, nystagmus, ataxia. Imaging based methods, e.g., those as disclosed above, can also be performed to confirm the presence of schwannoma.

Common symptoms of ependymoma include, but are not limited to, one or more of the following: severe headache, visual loss, vomiting, bilateral Babinski sign, drowsiness (after several hours of the above symptoms), gait change (rotation of feet when walking), and constipation. Imaging based methods, e.g., those as described above, can also be used to confirm the presence of ependymoma.

In some cases, a biopsy, often obtained at the time when the tumor is being surgically removed, is analyzed to further confirm the presence of NF 2, e.g., meningioma, schwannoma, or ependymoma.

E. Glucocorticoid Receptor Modulators (GRM)

Generally, treatment of an GR+ neuroepithelial tumor, e.g., schwannoma, meningioma, or ependymoma, can be provided by administering an effective amount of a SGRM of any chemical structure or mechanism of action. Provided herein, are classes of exemplary GRMs and specific members of such classes. However, one of skill in the art will readily recognize other related or unrelated SGRMs that can be employed in the treatment methods described herein.

1. GRMs Having a Steroidal Backbone

In some embodiments, an effective amount of a SGRM with a steroidal backbone is administered to a subject for cancer treatment. Steroidal GRMs can be obtained by modification of the basic structure of glucocorticoid agonists, i.e., varied forms of the steroid backbone. The structure of cortisol can be modified in a variety of ways. The two most commonly known classes of structural modifications of the cortisol steroid backbone to create GRMs include modifications of the 11-β hydroxy group and modification of the 17-β side chain (See, e.g., Lefebvre, J. Steroid Biochem. 33:557-563, 1989).

Examples of steroidal GRMs, including steroidal SGRMs, include androgen-type steroidal compounds as described in U.S. Pat. No. 5,929,058, and the compounds disclosed in U.S. Pat. Nos. 4,296,206; 4,386,085; 4,447,424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; 5,616,458, 5,696,127, and 6,303,591. Such steroidal GR antagonists include cortexolone, dexamethasone-oxetanone, 19-nordeoxycorticosterone, 19-norprogesterone, cortisol-21-mesylate; dexamethasone-21-mesylate, 11β-(4-dimethylaminoethoxyphenyl)-17α-propynyl-17β-hydroxy-4,9-estradien-3-one (RU009), and (17α)-17-hydroxy-19-(4-methylphenyl)androsta-4,9(11)-dien-3-one (RU044).

Other examples of steroidal antiglucocorticoids are disclosed in Van Kampen et al. (2002) Eur. J. Pharmacol. 457(2-3):207, WO 03/043640, EP 0 683 172 B1, and EP 0 763 541 B1, each of which is incorporated herein by reference. EP 0 763 541 B1 and Hoyberg et al., Int'l J. of Neuro-psychopharmacology, 5:Supp. 1, S148 (2002) disclose the compound (11β,17β)-11-(1,3-benzodioxol-5-yl)-17-hydroxy-17-(1-propynyl)estra-4,9-dien-3-one (ORG 34517), which in one embodiment, is administered in an amount effective to treat an ACTH-secreting tumor in a subject.

2. Removal or Substitution of the 11-β Hydroxy Group

GRMs, including SGRMs, with modified steroidal backbones comprising removal or substitution of the 11-β hydroxy group are administered in one embodiment of the methods disclosed herein. This class includes natural GRMs, including cortexolone, progesterone and testosterone derivatives, and synthetic compositions, such as mifepristone (Lefebvre, et al. supra). Preferred embodiments of the methods disclosed herein include all 11-β aryl steroid backbone derivatives because, in some cases, these compounds can be devoid of progesterone receptor (PR) binding activity (Agarwal, FEBS 217:221-226, 1987). In another embodiment an 11-β phenyl-aminodimethyl steroid backbone derivative, which is both an effective anti-glucocorticoid and anti-progesterone agent, is administered. These compositions can act as reversibly-binding steroid receptor antagonists. For example, when bound to a 11-β phenyl-aminodimethyl steroid, the steroid receptor can be maintained in a conformation that cannot bind its natural ligand, such as cortisol in the case of GR (Cadepond, 1997, supra).

Synthetic 11-beta phenyl-aminodimethyl steroids include mifepristone, also known as RU486, or 17-β-hydrox-11-β-(4-dimethyl-aminophenyl) 17-α-(1-propynyl)estra-4,9-dien-3-one). Mifepristone has been shown to be a powerful antagonist of both the progesterone and glucocorticoid (GR) receptors. Thus, in some embodiments, the GRM administered to treat a GR+ neuroepithelial tumor or an ACTH-secreting tumor is mifepristone, or a salt, tautomer, or derivative thereof. In other embodiments, however, administration of mifepristone is specifically excluded as a GRM for treatment of a GR+ neuroepithelial tumor. In other embodiments, however, administration of mifepristone is specifically excluded as a GRM for treatment of an ACTH-secreting tumor.

Another 11-β phenyl-aminodimethyl steroid shown to have GR antagonist effects includes the dimethyl aminoethoxyphenyl derivative RU009 (RU39,009), 11-β-(4-dimethyl-aminoethoxyphenyl)-17-α-(propynyl-17-β-hydroxy-4,9-estradien-3-one) (see Bocquel, J. Steroid Biochem. Mol. Biol. 45:205-215, 1993). Another GR antagonist related to RU486 is RU044 (RU43,044) 17-β-hydrox-17-α-19-(4-methyl-phenyl)-androsta-4,9(11)-dien-3-one) (Bocquel, 1993, supra). See also Teutsch, Steroids 38:651-665, 1981; U.S. Pat. Nos. 4,386,085 and 4,912,097.

One embodiment includes compositions that are irreversible anti-glucocorticoids. Such compounds include α-keto-methanesulfonate derivatives of cortisol, including cortisol-21-mesylate (4-pregnene-11-β, 17-α, 21-triol-3, 20-dione-21-methane-sulfonate and dexamethasone-21-mesylate (16-methyl-9-α-fluoro-1,4-pregnadiene-11β, 17-α, 21-triol-3, 20-dione-21-methane-sulfonate). See Simons, J. Steroid Biochem. 24:25-32, 1986; Mercier, J. Steroid Biochem. 25:11-20, 1986; U.S. Pat. No. 4,296,206.

3. Modification of the 17-Beta Side Chain Group

Steroidal anti-glucocorticoids which can be obtained by various structural modifications of the 17-β side chain are also used in the methods disclosed herein. This class includes synthetic antiglucocorticoids, such as dexamethasone-oxetanone, various 17, 21-acetonide derivatives and 17-beta-carboxamide derivatives of dexamethasone (Lefebvre, 1989, supra; Rousseau, Nature 279:158-160, 1979).

4. Other Steroid Backbone Modifications

GRMs, including SGRMs, used in the various embodiments of the methods disclosed herein include any steroid backbone modification which effects a biological response resulting from a GR-agonist interaction. Steroid backbone antagonists can be any natural or synthetic variation of cortisol, such as adrenal steroids missing the C-19 methyl group, such as 19-nordeoxycorticosterone and 19-norprogesterone (Wynne, Endocrinology 107:1278-1280, 1980).

In general, the 11-β side chain substituent, and particularly the size of that substituent, can play a key role in determining the extent of a steroid's antiglucocorticoid activity. Substitutions in the A ring of the steroid backbone can also be important. For example, 17-hydroxypropenyl side chains can, in some cases, decrease antiglucocorticoid activity in comparison to 17-propynyl side chain containing compounds.

Additional glucocorticoid receptor antagonists known in the art and suitable for practice of the methods disclosed herein include 21-hydroxy-6,19-oxidoprogesterone (See Vicent, Mol. Pharm. 52:749-753, 1997), Org31710 (See Mizutani, J Steroid Biochem Mol Biol 42(7):695-704, 1992), RU43044, RU40555 (See Kim, J Steroid Biochem Mol Biol. 67(3):213-22, 1998), and RU28362.

5. Nonsteroidal Anti-Glucocorticoid Receptors Modulators

Provided herein, are classes of exemplary nonsteroidal glucocorticoid receptor modulator (GRM) and specific members of such classes that can be used for the methods disclosed herein. Such nonsteroidal GRMs may be nonsteroidal SGRMs. However, one of skill in the art will readily recognize other related or unrelated glucocorticoid receptor modulators that can be employed in the treatment methods described herein. These include synthetic mimetics and analogs of proteins, including partially peptidic, pseudopeptidic and non-peptidic molecular entities. For example, oligomeric peptidomimetics useful in the methods disclosed herein include (α-β-unsaturated) peptidosulfonamides, N-substituted glycine derivatives, oligo carbamates, oligo urea peptidomimetics, hydrazinopeptides, oligosulfones and the like (See, e.g., Amour, Int. J. Pept. Protein Res. 43:297-304, 1994; de Bont, Bioorganic &Medicinal Chem. 4:667-672, 1996).

Examples of nonsteroidal GR modulators include the GR antagonist compounds disclosed in U.S. Pat. Nos. 5,696,127; 6,570,020; and 6,051,573; the GR antagonist compounds disclosed in US Patent Application 20020077356, the glucocorticoid receptor antagonists disclosed in Bradley et al., J. Med. Chem. 45, 2417-2424 (2002), e.g., 4α(S)-benzyl-2(R)-chloroethynyl-1,2,3,4,4a,9,10,10α(R)-octahydro-phenanthrene-2,7-diol ("CP 394531") and 4α(S)-benzyl-2(R)-prop-1-ynyl-1,2,3,4,4α,9,10,10α(R)-octahydro-phenanthrene-2,7-diol ("CP 409069"); and the compounds disclosed in PCT International Application No. WO 96/19458, which describes non-steroidal compounds which are high-affinity, highly selective antagonists for steroid receptors, such as 6-substituted-1,2-dihydro-N-protected-quinolines.

For additional compounds that can be utilized in the methods disclosed herein and in methods of identifying and making compounds useful in practicing these methods, see U.S. Pat. No. 4,296,206 (see above); U.S. Pat. No. 4,386,085 (see above); U.S. Pat. Nos. 4,447,424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; and 5,616,458; and WO 96/19458, which describes non-steroidal compounds which are high-affinity, highly selective modulators (antagonists) for steroid receptors, such as 6-substituted-1,2-dihydro N-1 protected quinolines.

In some embodiments, the combination therapy for treating cancer involves a nonsteroidal GRM having a fused azadecalin backbone, a heteroaryl ketone fused azadecalin backbone, or an octahydro fused azadecalin backbone.

Exemplary GRMs having a fused azadecalin backbone include those described in U.S. Pat. Nos. 7,928,237; 8,461,172; and 8,557,839, all three of which patents are hereby incorporated by reference in their entireties. In some cases, the GRM having a fused azadecalin backbone has the following structure:

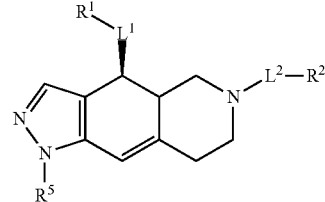

wherein $L^1$ and $L^2$ are members independently selected from a bond and unsubstituted alkylene;

$R^1$ is a member selected from unsubstituted alkyl, unsubstituted heteroalkyl, unsubstituted heterocycloalkyl, —$OR^{1A}$, —$NR^{1C}R^{1D}$, —$C(O)NR^{1C}R^{1D}$, and —$C(O)OR^{1A}$, wherein $R^{1A}$ is a member selected from hydrogen, unsubstituted alkyl and unsubstituted heteroalkyl, $R^{1C}$ and $R^{1D}$ are members independently selected from unsubstituted alkyl and unsubstituted heteroalkyl, wherein $R^{1C}$ and $R^{1D}$ are optionally joined to form an unsubstituted ring with the nitrogen to which they are attached, wherein said ring optionally comprises an additional ring nitrogen;

$R^2$ has the formula:

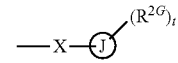

wherein
R[2G] is a member selected from hydrogen, halogen, unsubstituted alkyl, unsubstituted heteroalkyl, unsubstituted cycloalkyl, unsubstituted heterocycloalkyl, —CN, and —CF$_3$;
J is phenyl;
t is an integer from 0 to 5;
X is —S(O$_2$)—; and
R[5] is phenyl optionally substituted with 1-5 R[5A] groups, wherein
R[5A] is a member selected from hydrogen, halogen, —OR[5A1], —S(O$_2$)NR[5A2]R[5A3], —CN, and unsubstituted alkyl, wherein
R[5A1] is a member selected from hydrogen and unsubstituted alkyl, and
R[5A2] and R[5A3] are members independently selected from hydrogen and unsubstituted alkyl,
or salts and isomers thereof.

Compounds containing fused azadecalin backbones can be prepared as described in U.S. Pat. No. 7,928,237. For example, fused azadecalin backbones can be prepared as described in Scheme 1, where, R[5], R[1A], R[1C], R[1D], L[2] and R[2] are as defined above in the compounds useful in the practice of the methods disclosed herein. In Scheme 1, L[2]-R[2] can be replaced by a suitable protecting group, such as BOC or benzyl, to facilitate the synthesis. Keto-ester 1 is converted directly to enone 3 by a Robinson annelation reaction involving treatment of 1 with a base (e.g. potassium or sodium alkoxides) in an alcohol solvent (e.g. methanol, ethanol, or tert-butanol) followed by addition of methylvinyl ketone (MVK). The reaction is typically carried out at 0-250° C.

by reference herein in its entirety. In some cases, the GRM having a heteroaryl ketone fused azadecalin backbone has the following structure:

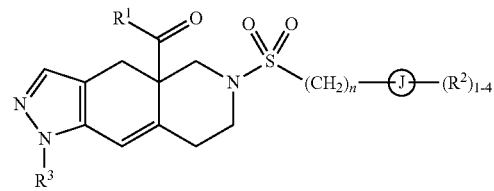

wherein
R[1] is a heteroaryl ring having from 5 to 6 ring members and from 1 to 4 heteroatoms each independently selected from the group consisting of N, O and S, optionally substituted with 1-4 groups each independently selected from R[1a];
each R[1a] is independently selected from the group consisting of hydrogen, C$_{1-6}$ alkyl, halogen, C$_{1-6}$ haloalkyl, C$_{1-6}$ alkoxy, C$_{1-6}$ haloalkoxy, —CN, N-oxide, C$_{3-8}$ cycloalkyl, and C$_{3-8}$ heterocycloalkyl;
ring J is selected from the group consisting of a cycloalkyl ring, a heterocycloalkyl ring, an aryl ring and a heteroaryl ring, wherein the heterocycloalkyl and heteroaryl rings have from 5 to 6 ring members and from 1 to 4 heteroatoms each independently selected from the group consisting of N, O and S;
each R[2] is independently selected from the group consisting of hydrogen, C$_{1-6}$ alkyl, halogen, C$_{1-6}$ haloalkyl,

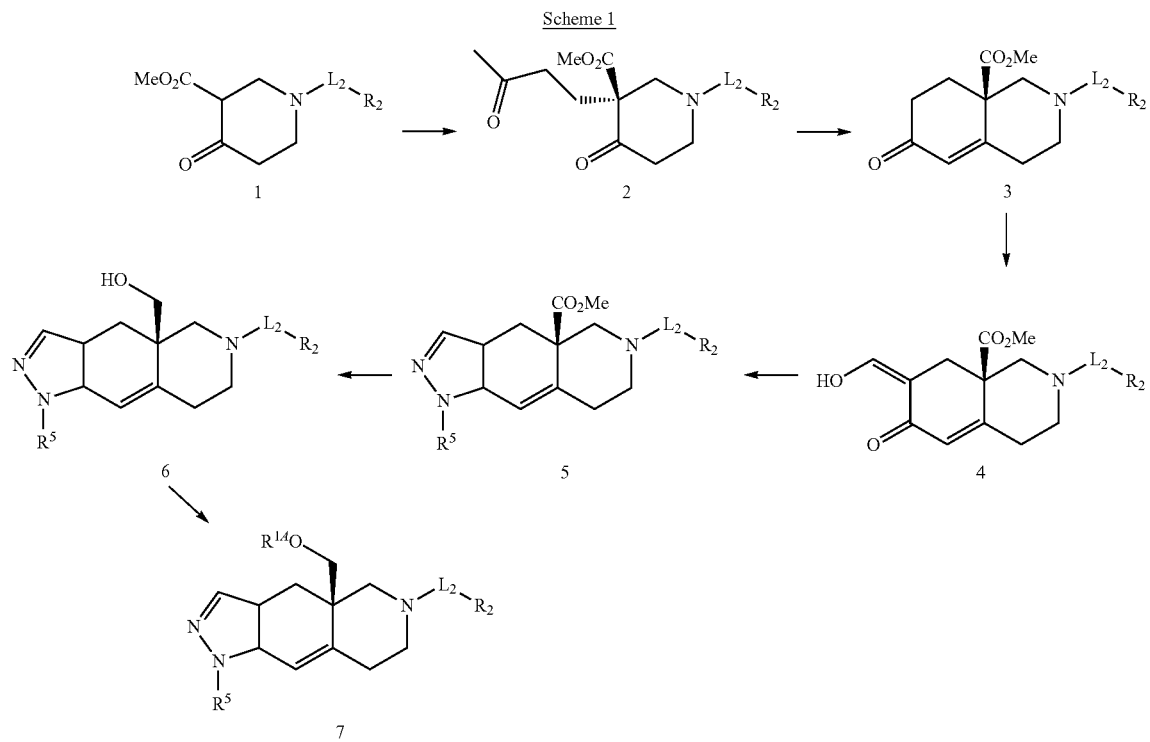

Exemplary GRMs having a heteroaryl ketone fused azadecalin backbone include those described in U.S. 2014/0038926, now U.S. Pat. No. 8,859,774, hereby incorporated C$_{1-6}$ alkoxy, C$_{1-6}$ haloalkoxy, C$_{1-6}$ alkyl-C$_{1-6}$ alkoxy, —CN, —OH, —NR[2a]R[2b], —C(O)R[2a], —C(O)OR[2a], —C(O)NR[2a]R[2b], —SR[2a], —S(O)R[2a], —S(O)$_2$ R[2a], $C_{3-8}$ cycloalkyl, and $C_{3-8}$ heterocycloalkyl, wherein the heterocycloalkyl groups are optionally substituted with 1-4 $R^{2c}$ groups;

alternatively, two $R^2$ groups linked to the same carbon are combined to form an oxo group (=O);

alternatively, two $R^2$ groups are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2d}$ groups;

$R^{2a}$ and $R^{2b}$ are each independently selected from the group consisting of hydrogen and $C_{1-6}$ alkyl;

each $R^{2c}$ is independently selected from the group consisting of hydrogen, halogen, hydroxy, $C_{1-6}$ alkoxy, $C_{1-6}$ haloalkoxy, —CN, and —$NR^{2a}R^{2b}$;

each $R^{2d}$ is independently selected from the group consisting of hydrogen and $C_{1-6}$ alkyl, or two $R^{2d}$ groups attached to the same ring atom are combined to form (=O);

$R^3$ is selected from the group consisting of phenyl and pyridyl, each optionally substituted with 1-4 $R^{3a}$ groups;

each $R^{3a}$ is independently selected from the group consisting of hydrogen, halogen, and $C_{1-6}$ haloalkyl; and subscript n is an integer from 0 to 3;

or salts and isomers thereof.

Compounds containing fused azadecalin backbones can be prepared as described in Scheme 2.

Exemplary GRMs having an octahydro fused azadecalin backbone include those described in U.S. patent application Ser. No. 14/549,885, entitled Octahydro Fused Azadecalin Glucocorticoid Receptor Modulators, published as U.S. Patent Publication 2015-0148341, the entire contents of which is hereby incorporated by reference herein in its entirety. In some cases, the GRM having an octahydro fused azadecalin backbone has the following structure:

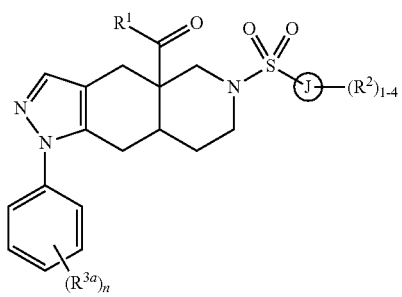

wherein $R^1$ is a heteroaryl ring having from 5 to 6 ring members and from 1 to 4 heteroatoms each independently selected from the group consisting of N, O and S, optionally substituted with 1-4 groups each independently selected from $R^{1a}$;

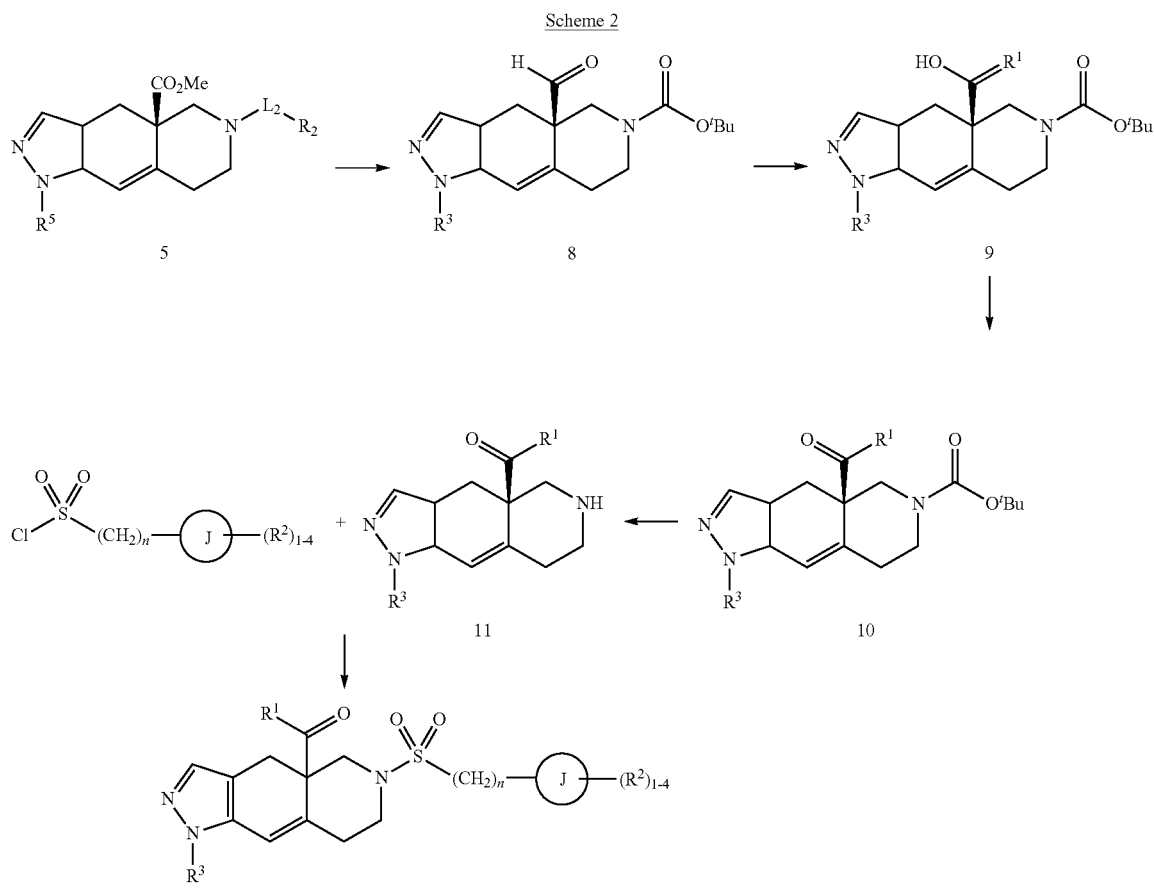

Scheme 2 each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, N-oxide, and $C_{3-8}$ cycloalkyl;

ring J is selected from the group consisting of an aryl ring and a heteroaryl ring having from 5 to 6 ring members and from 1 to 4 heteroatoms each independently selected from the group consisting of N, O and S;

each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —OH, —$NR^{2a}R^{2b}$, —$C(O)R^{2a}$, —$C(O)OR^{2a}$, —$C(O)NR^{2a}R^{2b}$, —$SR^{2a}$, —$S(O)R^{2a}$, —$S(O)_2 R^{2a}$, $C_{3-8}$ cycloalkyl, and $C_{3-8}$ heterocycloalkyl having from 1 to 3 heteroatoms each independently selected from the group consisting of N, O and S;

alternatively, two $R^2$ groups on adjacent ring atoms are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2c}$ groups;

$R^{2a}$, $R^{2b}$ and $R^{2c}$ are each independently selected from the group consisting of hydrogen and $C_{1-6}$ alkyl;

each $R^{3a}$ is independently halogen; and subscript n is an integer from 0 to 3;

or salts and isomers thereof.

Compounds containing octahydro fused azadecalin backbones can be prepared as described in Scheme 3.

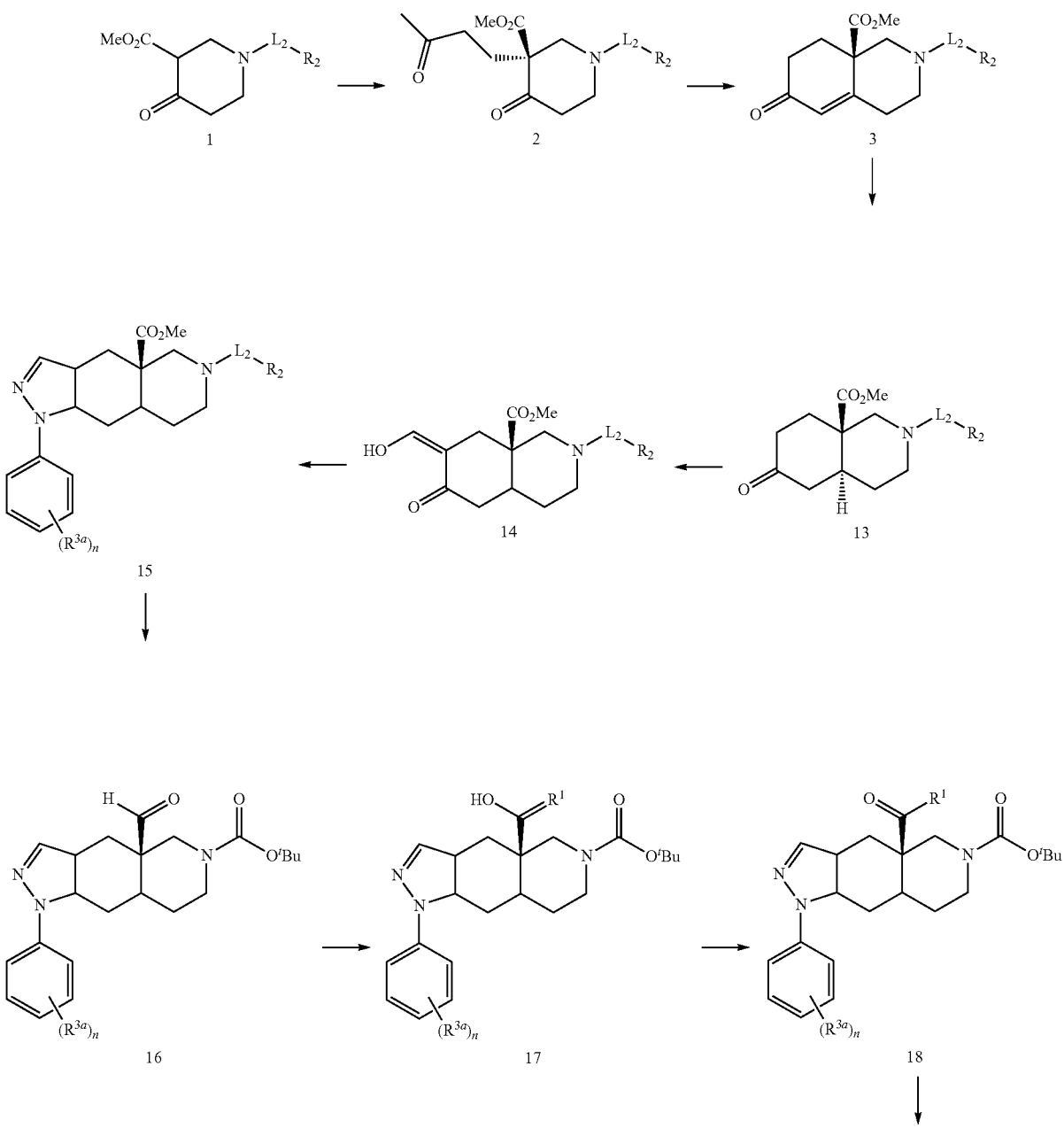

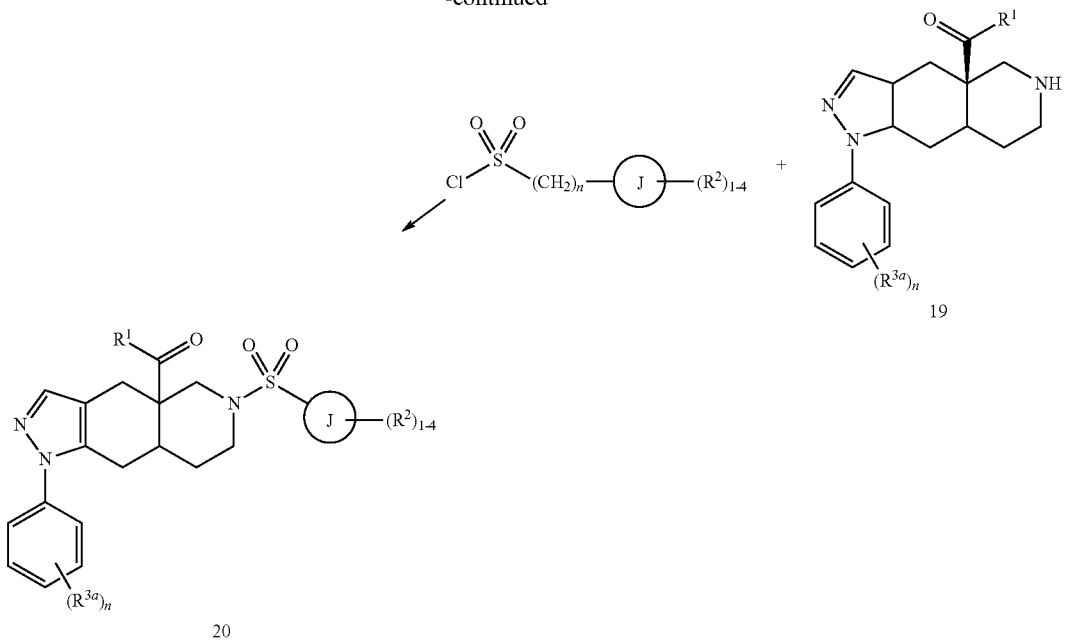

F. Identifying Selective Glucocorticoid Receptor Modulators (SGRMS)

To determine whether a test compound is a SGRM, the compound is first subjected to assays to measure its ability to bind to the GR and inhibit GR-mediated activities, which determines whether the compound is a glucocorticoid receptor modulator. The compound, if confirmed to be a glucocorticoid receptor modulator, is then subjected to a selectivity test to determine whether the compound can bind specifically to GR as compared to non-GR proteins, such as the estrogen receptor, the progesterone receptor, the androgen receptor, or the mineralocorticoid receptor. In one embodiment, a SGRM binds to GR at a substantially higher affinity, e.g., at least 10 times higher affinity, than to non-GR proteins. A SGRM may exhibit a 100 fold, 1000 fold or greater selectivity for binding to GR relative to binding to non-GR proteins.

i. Binding

A test compounds' ability to bind to the glucocorticoid receptor can be measured using a variety of assays, for example, by screening for the ability of the test compound to compete with a glucocorticoid receptor ligand, such as dexamethasone, for binding to the glucocorticoid receptor. Those of skill in the art will recognize that there are a number of ways to perform such competitive binding assays. In some embodiments, the glucocorticoid receptor is pre-incubated with a labeled glucocorticoid receptor ligand and then contacted with a test compound. This type of competitive binding assay may also be referred to herein as a binding displacement assay. A decrease of the quantity of labeled ligand bound to glucocorticoid receptor indicates that the test compound binds to the glucocorticoid receptor. In some cases, the labeled ligand is a fluorescently labeled compound (e.g., a fluorescently labeled steroid or steroid analog). Alternatively, the binding of a test compound to the glucocorticoid receptor can be measured directly with a labeled test compound. This latter type of assay is called a direct binding assay.

Both direct binding assays and competitive binding assays can be used in a variety of different formats. The formats may be similar to those used in immunoassays and receptor binding assays. For a description of different formats for binding assays, including competitive binding assays and direct binding assays, see *Basic and Clinical Immunology* 7th Edition (D. Stites and A. Terr ed.) 1991; *Enzyme Immunoassay*, E. T. Maggio, ed., CRC Press, Boca Raton, Fla. (1980); and "Practice and Theory of Enzyme Immunoassays," P. Tijssen, *Laboratory Techniques in Biochemistry and Molecular Biology*, Elsevier Science Publishers B.V. Amsterdam (1985), each of which is incorporated herein by reference.

In solid phase competitive binding assays, for example, the sample compound can compete with a labeled analyte for specific binding sites on a binding agent bound to a solid surface. In this type of format, the labeled analyte can be a glucocorticoid receptor ligand and the binding agent can be glucocorticoid receptor bound to a solid phase. Alternatively, the labeled analyte can be labeled glucocorticoid receptor and the binding agent can be a solid phase glucocorticoid receptor ligand. The concentration of labeled analyte bound to the capture agent is inversely proportional to the ability of a test compound to compete in the binding assay.

Alternatively, the competitive binding assay may be conducted in the liquid phase, and any of a variety of techniques known in the art may be used to separate the bound labeled protein from the unbound labeled protein. For example, several procedures have been developed for distinguishing between bound ligand and excess bound ligand or between bound test compound and the excess unbound test compound. These include identification of the bound complex by sedimentation in sucrose gradients, gel electrophoresis, or gel isoelectric focusing; precipitation of the receptor-ligand complex with protamine sulfate or adsorption on hydroxylapatite; and the removal of unbound compounds or ligands by adsorption on dextran-coated charcoal (DCC) or binding to immobilized antibody. Following separation, the amount of bound ligand or test compound is determined.

Alternatively, a homogenous binding assay may be performed in which a separation step is not needed. For example, a label on the glucocorticoid receptor may be altered by the binding of the glucocorticoid receptor to its ligand or test compound. This alteration in the labeled glucocorticoid receptor results in a decrease or increase in the signal emitted by label, so that measurement of the label at the end of the binding assay allows for detection or quantitation of the glucocorticoid receptor in the bound state. A wide variety of labels may be used. The component may be labeled by any one of several methods. Useful radioactive labels include those incorporating $^3H$, $^{125}I$, $^{35}S$, $^{14}C$, or $^{32}P$. Useful non-radioactive labels include those incorporating fluorophores, chemiluminescent agents, phosphorescent agents, electrochemiluminescent agents, and the like. Fluorescent agents are especially useful in analytical techniques that are used to detect shifts in protein structure such as fluorescence anisotropy and/or fluorescence polarization. The choice of label depends on sensitivity required, case of conjugation with the compound, stability requirements, and available instrumentation. For a review of various labeling or signal producing systems which may be used, see U.S. Pat. No. 4,391,904, which is incorporated herein by reference in its entirety for all purposes. The label may be coupled directly or indirectly to the desired component of the assay according to methods well known in the art. In some cases, a test compound is contacted with a GR in the presence of a fluorescently labeled ligand (e.g., a steroid or steroid analog) with a known affinity for the GR, and the quantity of bound and free labeled ligand is estimated by measuring the fluorescence polarization of the labeled ligand.

ii. Activity

1) HepG2 Tyrosine Aminotransferase (TAT) Assay

Compounds that have demonstrated the desired binding affinity to GR are tested for their activity in inhibiting GR mediated activities. The compounds are typically subject to a Tyrosine Aminotransferase Assay (TAT), which assesses the ability of a test compound to inhibit the induction of tyrosine aminotransferase activity by dexamethasone. See Example 1. GR modulators that are suitable for the method disclosed herein have an $IC_{50}$ (half maximal inhibition concentration) of less than 10 micromolar. Other assays, including but not limited to those described below, can also be deployed to confirm the GR modulation activity of the compounds.

2) Cell-Based Assays

Cell-based assays which involve whole cells or cell fractions containing glucocorticoid receptors can also be used to assay for a test compound's binding or modulation of activity of the glucocorticoid receptor. Exemplary cell types that can be used according to the methods disclosed herein include, e.g., any mammalian cells including leukocytes such as neutrophils, monocytes, macrophages, eosinophils, basophils, mast cells, and lymphocytes, such as T cells and B cells, leukemia cells, Burkitt's lymphoma cells, tumor cells (including mouse mammary tumor virus cells), endothelial cells, fibroblasts, cardiac cells, muscle cells, breast tumor cells, ovarian cancer carcinomas, cervical carcinomas, glioblastomas, liver cells, kidney cells, and neuronal cells, as well as fungal cells, including yeast. Cells can be primary cells or tumor cells or other types of immortal cell lines. Of course, the glucocorticoid receptor can be expressed in cells that do not express an endogenous version of the glucocorticoid receptor.

In some cases, fragments of the glucocorticoid receptor, as well as protein fusions, can be used for screening. When molecules that compete for binding with the glucocorticoid receptor ligands are desired, the GR fragments used are fragments capable of binding the ligands (e.g., dexamethasone). Alternatively, any fragment of GR can be used as a target to identify molecules that bind the glucocorticoid receptor. Glucocorticoid receptor fragments can include any fragment of, e.g., at least 20, 30, 40, 50 amino acids up to a protein containing all but one amino acid of glucocorticoid receptor.

In some embodiments, a reduction in signaling triggered by glucocorticoid receptor activation is used to identify glucocorticoid receptor modulators. Signaling activity of the glucocorticoid receptor can be determined in many ways. For example, downstream molecular events can be monitored to determine signaling activity. Downstream events include those activities or manifestations that occur as a result of stimulation of a glucocorticoid receptor. Exemplary downstream events useful in the functional evaluation of transcriptional activation and antagonism in unaltered cells include upregulation of a number of glucocorticoid response element (GRE)-dependent genes (PEPCK, tyrosine amino transferase, aromatase). In addition, specific cell types susceptible to GR activation may be used, such as osteocalcin expression in osteoblasts which is downregulated by glucocorticoids; primary hepatocytes which exhibit glucocorticoid mediated upregulation of PEPCK and glucose-6-phosphate (G-6-Pase)). GRE-mediated gene expression has also been demonstrated in transfected cell lines using well-known GRE-regulated sequences (e.g., the mouse mammary tumor virus promoter (MMTV) transfected upstream of a reporter gene construct). Examples of useful reporter gene constructs include luciferase (luc), alkaline phosphatase (ALP) and chloramphenicol acetyl transferase (CAT). The functional evaluation of transcriptional repression can be carried out in cell lines such as monocytes or human skin fibroblasts. Useful functional assays include those that measure IL-1beta stimulated IL-6 expression; the downregulation of collagenase, cyclooxygenase-2 and various chemokines (MCP-1, RANTES); LPS stimulated cytokine release, e.g., TNFα; or expression of genes regulated by NFkB or AP-1 transcription factors in transfected cell-lines.

Compounds that are tested in whole-cell assays can also be tested in a cytotoxicity assay. Cytotoxicity assays are used to determine the extent to which a perceived effect is due to non-glucocorticoid receptor binding cellular effects. In an exemplary embodiment, the cytotoxicity assay includes contacting a constitutively active cell with the test compound. Any decrease in cellular activity indicates a cytotoxic effect.

3) Additional Assays

Further illustrative of the many assays which can be used to identify compositions utilized in the methods disclosed herein, are assays based on glucocorticoid activities in vivo. For example, assays that assess the ability of a putative GR modulator to inhibit uptake of 3H-thymidine into DNA in cells which are stimulated by glucocorticoids can be used. Alternatively, the putative GR modulator can complete with 3H-dexamethasone for binding to a hepatoma tissue culture GR (see, e.g., Choi, et al., *Steroids* 57:313-318, 1992). As another example, the ability of a putative GR modulator to block nuclear binding of 3H-dexamethasone-GR complex can be used (Alexandrova et al., *J. Steroid Biochem. Mol. Biol.* 41:723-725, 1992). To further identify putative GR modulators, kinetic assays able to discriminate between glucocorticoid agonists and modulators by means of receptor-binding kinetics can also be used (as described in Jones, *Biochem J.* 204:721-729, 1982).

In another illustrative example, the assay described by Daune, Molec. Pharm. 13:948-955, 1977; and in U.S. Pat. No. 4,386,085, can be used to identify anti-glucocorticoid activity. Briefly, the thymocytes of adrenalectomized rats are incubated in nutritive medium containing dexamethasone with the test compound (the putative GR modulator) at varying concentrations. $^3$H-uridine is added to the cell culture, which is further incubated, and the extent of incorporation of radiolabel into polynucleotide is measured. Glucocorticoid agonists decrease the amount of $^3$H-uridine incorporated. Thus, a GR modulator will oppose this effect.

iii. Selectivity

The GR modulators selected above are then subject to a selectivity assay to determine whether they are SGRMs. Typically, selectivity assays include testing a compound that binds glucocorticoid receptor in vitro for the degree of binding to non-glucocorticoid receptor proteins. Selectivity assays may be performed in vitro or in cell based systems, as described above. Binding may be tested against any appropriate non-glucocorticoid receptor protein, including antibodies, receptors, enzymes, and the like. In an exemplary embodiment, the non-glucocorticoid receptor binding protein is a cell-surface receptor or nuclear receptor. In another exemplary embodiment, the non-glucocorticoid receptor protein is a steroid receptor, such as estrogen receptor, progesterone receptor, androgen receptor, or mineralocorticoid receptor.

The selectivity of the antagonist for the GR relative to the MR can be measured using a variety of assays known to those of skill in the art. For example, specific antagonists can be identified by measuring the ability of the antagonist to bind to the GR compared to the MR (see, e.g., U.S. Pat. Nos. 5,606,021; 5,696,127; 5,215,916; and 5,071,773). Such an analysis can be performed using either a direct binding assay or by assessing competitive binding to the purified GR or MR in the presence of a known ligand. In an exemplary assay, cells that stably express the glucocorticoid receptor or mineralocorticoid receptor (see, e.g., U.S. Pat. No. 5,606,021) at high levels are used as a source of purified receptor. The affinity of the ligand for the receptor is then directly measured. Those GR modulators that exhibit at least a 10-fold, a 100-fold higher affinity, and often a 1000-fold higher affinity, for the GR relative to the MR are then selected for use in the methods disclosed herein.

The selectivity assay may also include assaying the ability to inhibit GR-mediated activities, but not MR-mediated activities. One method of identifying such a GR-specific modulator is to assess the ability of an antagonist to prevent activation of reporter constructs using transfection assays (see, e.g., Bocquel et al, J. Steroid Biochem Molec. Biol. 45:205-215, 1993; U.S. Pat. Nos. 5,606,021, 5,929,058). In an exemplary transfection assay, an expression plasmid encoding the receptor and a reporter plasmid containing a reporter gene linked to receptor-specific regulatory elements are co-transfected into suitable receptor-negative host cells. The transfected host cells are then cultured in the presence and absence of a hormone, such as cortisol or an analog thereof, able to activate the hormone responsive promoter/enhancer element of the reporter plasmid. Next the transfected and cultured host cells are monitored for induction (i.e., the presence) of the product of the reporter gene sequence. Finally, the expression and/or steroid binding-capacity of the hormone receptor protein (coded for by the receptor DNA sequence on the expression plasmid and produced in the transfected and cultured host cells), is measured by determining the activity of the reporter gene in the presence and absence of an antagonist. The antagonist activity of a compound may be determined in comparison to known antagonists of the GR and MR receptors (see, e.g., U.S. Pat. No. 5,696,127). Efficacy is then reported as the percent maximal response observed for each compound relative to a reference antagonist compound. GR modulators that exhibits at least a 100-fold, often 1000-fold or greater, activity towards the GR relative to the MR, PR, or AR are then selected for use in the methods disclosed herein.

An exemplar SGRM that can be used in the methods disclosed herein is CORT125134, i.e., (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone, which has the following structure:

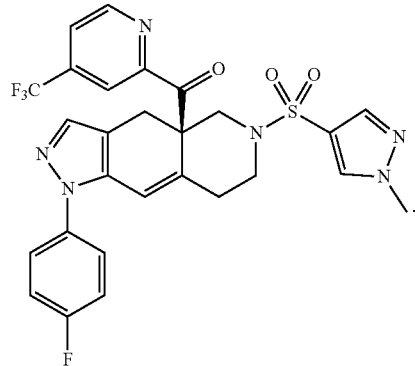 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

Another exemplar SGRM that can be used in the methods disclosed herein is CORT125281, i.e., ((4aR,8aS)-1-(4-fluorophenyl)-6-((2-methyl-2H-1,2,3-triazol-4-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone, which has the following structure:

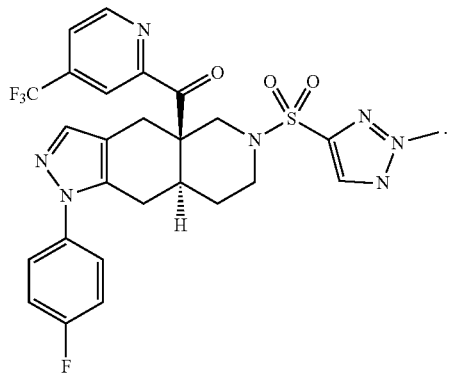

G. Pharmaceutical Compositions and Administration

In some embodiments, a pharmaceutical composition including a pharmaceutically acceptable excipient and a nonsteroidal GRM are useful in the practice of the methods disclosed herein.

Nonsteroidal GRMs can be prepared and administered in a wide variety of oral, parenteral and topical dosage forms.

Oral preparations include tablets, pills, powder, dragees, capsules, liquids, lozenges, gels, syrups, slurries, suspensions, etc., suitable for ingestion by the patient. Nonsteroidal GRMs can also be administered by injection, that is, intravenously, intramuscularly, intracutaneously, subcutaneously, intraduodenally, or intraperitoneally. Also, nonsteroidal GRMs can be administered by inhalation, for example, intranasally. Additionally, nonsteroidal GRMs can be administered transdermally. Accordingly, pharmaceutical compositions including a pharmaceutically acceptable carrier or excipient and a nonsteroidal GRM are useful in the practice of the methods disclosed herein.

For preparing pharmaceutical compositions from nonsteroidal GRMs, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Mack Publishing Co, Easton Pa. ("Remington's").

In powders, the carrier is a finely divided solid, which is in a mixture with the finely divided active component, a nonsteroidal GRM. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Suitable solid excipients are carbohydrate or protein tillers include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations useful for the practice of the methods pharmaceutical compositions including a pharmaceutically acceptable carrier or excipient and a nonsteroidal GRM can also be used orally using, for example, push-fit capsules made of gelatin, as well as soft, sealed capsules made of gelatin and a coating such as glycerol or sorbitol. Push-fit capsules can contain GR modulator mixed with a filler or binders such as lactose or starches, lubricants such as talc or magnesium stearate, and, optionally, stabilizers. In soft capsules, the GR modulator compounds may be dissolved or suspended in suitable liquids, such as fatty oils, liquid paraffin, or liquid polyethylene glycol with or without stabilizers.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending a nonsteroidal GRM in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations useful in the practice of the methods disclosed herein can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

Nonsteroidal GRMs can be delivered by transdermally, by a topical route, formulated as applicator sticks, solutions, suspensions, emulsions, gels, creams, ointments, pastes, jellies, paints, powders, and aerosols.

Nonsteroidal GRAs can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The pharmaceutical formulations useful in the practice of the methods disclosed herein can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH1 range of 4.5 to 5.5, that is combined with buffer prior to use In another embodiment, the formulations useful in the practice of the methods disclosed herein can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the GR modulator into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

The pharmaceutical preparation is preferably in unit dosage form. In such form the preparation is subdivided into unit doses containing appropriate quantities of the active component, a nonsteroidal GRA. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 6000 mg, most typically 600 mg to 1200 mg. Suitable dosages also include about 1 mg, 5, 10, 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, or 2000 mg, according to the particular application and the potency of the active component. The composition can, if desired, also contain other compatible therapeutic agents.

Single or multiple administrations of formulations can be administered depending on the dosage and frequency as required and tolerated by the patient. The formulations should provide a sufficient quantity of active agent to effectively treat the disease state. Thus, in one embodiment, the pharmaceutical formulation for oral administration of a nonsteroidal GRM is in a daily amount of between about 0.01 to about 150 mg per kilogram of body weight per day (mg/kg/day). In some embodiments, the daily amount is from about 1.0 to 100 mg/kg/day, 5 to 50 mg/kg/day, 10 to 30 mg/kg/day, and 10 to 20 mg/kg/day. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable formulations will be known or apparent to those skilled in the art and are described in more detail in such publications as Remington's, supra. See also Nieman, In "Receptor Mediated Antisteroid Action," Agarwal, et al., eds., De Gruyter, New York (1987).

The duration of treatment with nonsteroidal GRMs to reduce the tumor load of NF 2, e.g., meningioma or schwannoma or otherwise ameliorate the symptoms of these tumors can vary according to the severity of the condition in a subject and the subject's response to nonsteroidal GRMs. In some embodiments, nonsteroidal GRMs can be administered for a period of about 1 week to 104 weeks (2 years), more typically about 6 weeks to 80 weeks, most typically about 9 to 60 weeks. Suitable periods of administration also include 5 to 9 weeks, 5 to 16 weeks, 9 to 16 weeks, 16 to 24 weeks, 16 to 32 weeks, 24 to 32 weeks, 24 to 48 weeks, 32 to 48 weeks, 32 to 52 weeks, 48 to 52 weeks, 48 to 64 weeks, 52 to 64 weeks, 52 to 72 weeks, 64 to 72 weeks, 64 to 80 weeks, 72 to 80 weeks, 72 to 88 weeks, 80 to 88 weeks, 80 to 96 weeks, 88 to 96 weeks, and 96 to 104 weeks. Suitable periods of administration also include 5, 6, 7, 8, 9, 10, 11, 12, 13, 14, 15, 16, 17, 18, 19, 20, 24, 25, 30, 32, 35, 40, 45, 48, 50, 52, 55, 60, 64, 65, 68, 70, 72, 75, 80, 85, 88, 90, 95, 96, 100, and 104 weeks. Generally administration of a nonsteroidal GRM should be continued until clinically significant reduction or amelioration is observed. Treatment with a nonsteroidal GRM in accordance with the methods disclosed herein may last for as long as two years or even longer.

In some embodiments, administration of a nonsteroidal GRM is not continuous and can be stopped for one or more periods of time, followed by one or more periods of time where administration resumes. Suitable periods where administration stops include 5 to 9 weeks, 5 to 16 weeks, 9 to 16 weeks, 16 to 24 weeks, 16 to 32 weeks, 24 to 32 weeks, 24 to 48 weeks, 32 to 48 weeks, 32 to 52 weeks, 48 to 52 weeks, 48 to 64 weeks, 52 to 64 weeks, 52 to 72 weeks, 64 to 72 weeks, 64 to 80 weeks, 72 to 80 weeks, 72 to 88 weeks, 80 to 88 weeks, 80 to 96 weeks, 88 to 96 weeks, and 96 to 100 weeks. Suitable periods where administration stops also include 5, 6, 7, 8, 9, 10, 11, 12, 13, 14, 15, 16, 17, 18, 19, 20, 24, 25, 30, 32, 35, 40, 45, 48 50, 52, 55, 60, 64, 65, 68, 70, 72, 75, 80, 85, 88 90, 95, 96, and 100 weeks.

The dosage regimen also takes into consideration pharmacokinetics parameters well known in the art, i.e., the rate of absorption, bioavailability, metabolism, clearance, and the like (see, e.g., Hidalgo-Aragones (1996) *J. Steroid Biochem. Mol. Biol.* 58:611-617; Groning (1996) *Pharmazie* 51:337-341; Fotherby (1996) *Contraception* 54:59-69; Johnson (1995) *J. Pharm. Sci.* 84:1144-1146; Rohatagi (1995) *Pharmazie* 50:610-613; Brophy (1983) *Eur. J. Clin. Pharmacol.* 24:103-108; the latest Remington's, supra). The state of the art allows the clinician to determine the dosage regimen for each individual patient, GR modulator and disease or condition treated.

Nonsteroidal GRMs can be used in combination with other active agents known to be useful in modulating a glucocorticoid receptor, or with adjunctive agents that may not be effective alone, but may contribute to the efficacy of the active agent.

In some embodiments, co-administration includes administering one active agent, a nonsteroidal GRM, within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

After a pharmaceutical composition including a GRM has been formulated in an acceptable carrier, it can be placed in an appropriate container and labeled for treatment of an indicated condition. For administration of a nonsteroidal GRM, such labeling would include, e.g., instructions concerning the amount, frequency and method of administration.

The pharmaceutical compositions useful in the practice of the methods disclosed herein can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

In another embodiment, compositions useful in the practice of the methods disclosed herein are useful for parenteral administration, such as intravenous (IV) administration or administration into a body cavity or lumen of an organ. The formulations for administration will commonly comprise a solution of the compositions useful in the practice of the methods disclosed herein dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions useful in the practice of the methods disclosed herein in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

H. Combination Therapies

Also included in the methods disclosed herein are combination therapies for treating NF 2, e.g., meningioma or schwannoma, comprising a SGRM and one more conventional cancer therapies, such as, chemical or radiation based treatments, other therapeutic agents, and surgery, as those disclosed in US2011269728, the relevant disclosure is herein incorporated by reference in its entirety. Non-limiting examples of chemotherapies include temozolamide, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabine, navelbine, farnesyl-protein, transferase inhibitors, transplatinum, 5-fluorouracil, vincristin, vinblastin and methotrexate, or any analog or derivative variant of the foregoing. In some embodiments the chemotherapy agent is a composition comprising nanoparticles comprising a thiocolchicine derivative and a carrier protein (such as albumin). In further embodiments a combination of chemotherapeutic agents is administered to tumor cells. The chemotherapeutic agents may be administered serially (within minutes, hours, or days of each other) or in parallel; they also may be administered to the patient in a premixed single composition. Non-limiting examples of radiation therapies include Y-rays and x-rays.

Suitable therapeutic agents include, for example, vinca alkaloids, agents that disrupt microtubule formation (such as colchicines and its derivatives), anti-angiogenic agents, e.g. anti-VEGF antibodies (such as bevacizumab), therapeutic antibodies, EGFR targeting agents, tyrosine kinase targeting agent (such as tyrosine kinase inhibitors), serine kinase targeting agents, transitional metal complexes, proteasome inhibitors, antimetabolites (such as nucleoside analogs), alkylating agents, platinum-based agents, anthracycline antibiotics, topoisomerase inhibitors, macrolides, therapeutic antibodies, retinoids (such as alltrans retinoic acids or a derivatives thereof); geldanamycin or a derivative thereof (such as 17-AAG), and other standard chemotherapeutic agents well recognized in the art. As one embodiment, the methods disclosed herein expressly proviso out the combination of SGRM and somatostatin or its derivatives from the methods disclosed herein.

Various combinations with a SGRM and an anticancer agent or compound (or a combination of such agents and compounds) may be employed to reduce the tumor load in the patient. The SGRM and the anticancer agent or compound can be administered following the same or different dosing regimen. In some embodiments, the SGRM and the anticancer agent or compound is administered sequentially in any order during the entire or portions of the treatment period. In some embodiments, the SGRM and the anticancer agent is administered simultaneously or approximately simultaneously (e.g., within about 1, 5, 10, 15, 20, or 30 minutes of each other). Non-limiting examples of combination therapies are as follows, with administration of the SGRM and the anticancer agent for example, SGRM is "A" and the anticancer agent or compound, given as part of an anticancer therapy regime, is "B":

| | | | | | |
|---|---|---|---|---|---|
| A/B/AB | A/BB | B/AA | A/BA | B/BA | A/AA/B/B B/A/B/B |
| | B/B/B/A | B/B/A/B | A/A/B/B | A/B/A/B | A/B/B/A |
| B/B/A/A | | | | | |
| | B/A/B/A | B/A/A/B | A/A/A/B | B/A/A/A | A/B/A/A |
| A/A/B/A | | | | | |

Administration of the therapeutic compounds or agents to a patient will follow general protocols for the administration of such compounds, taking into account the toxicity, if any, of the therapy. Surgical intervention may also be applied in combination with the described therapy.

I. Evaluate Improvements in Reducing Tumor Loads

The SGRM therapy disclosed herein can reduce the tumor load and confer beneficial clinical outcome to patients having NF 2, e.g., meningioma or schwannoma. Methods for measuring these responses are well-known to skilled artisans in the field of cancer therapy, e.g., as described in the Response Evaluation Criteria in Solid Tumors ("RE-CIST") guidelines, as described in the PDF named "protocolDevelopment/docs/recist_guideline.pdf" available at etep.cancer.gov, and in the "Endpoints: How the Results of Clinical Trials are Measured" html article available at www.cancerguide.org.

In one approach, the tumor load is measured by assaying expression of tumor-specific genetic markers. This approach is especially useful for metastatic tumors. A tumor-specific genetic marker is a protein or other molecule that is unique to cancer cells or is much more abundant in them as compared to non-cancer cells. Useful tumor biomarkers for schwannoma are known, for example, VEGF and those described in Toren et al., Human Genomics 2014 (8): 10. Useful tumor biomarkers for meningitis are also known, for example, those described in Stuart et al., J. Neurol. 70(1):10 (2011).

Methods of measuring the expression levels of a tumor-specific genetic marker are well known. In some embodiments, mRNA of the genetic marker is isolated from the blood sample or a tumor tissue and real-time reverse transcriptase-polymerase chain reaction (RT-PCR) is performed to quantify expression of the genetic marker. In some embodiments, western blots or immunohistochemistry analysis are performed to evaluate the protein expression of the tumor-specific genetic marker. Typically the levels of the tumor-specific genetic marker are measured in multiple samples taken over time of the combination therapy methods disclosed herein, and a decrease in levels correlates with a reduction in tumor load.

In another approach, the reduction of tumor load by the combination therapy disclosed herein is shown by a reduction in tumor size or a reduction of amount of cancer in the body. Measuring tumor size is typically achieved by imaging-based techniques. For example, computed tomography (CT) scan can provide accurate and reliable anatomic information about not only tumor shrinkage or growth but also progression of disease by identifying either growth in existing lesions or the development of new lesions or tumor metastasis.

In yet another approach, a reduction of tumor load can be assessed by functional and metabolic imaging techniques. These techniques can provide earlier assessment of therapy response by observing alterations in perfusion, oxygenation and metabolism. For example, $^{18}$F-FDG PET uses radiolabelled glucose analogue molecules to assess tissue metabolism. Tumors typically have an elevated uptake of glucose, a change in value corresponding to a decrease in tumor tissue metabolism indicates a reduction in tumor load. Similar imaging techniques are disclosed in Kang et al., Korean J. Radiol. (2012) 13(4) 371-390.

A patient receiving the therapy disclosed herein may exhibit varying degrees of tumor load reduction. In some cases, a patient can exhibit a Complete Response (CR), also referred to as "no evidence of disease (NED)". CR means all detectable tumor has disappeared as indicated by tests, physical exams and scans. In some cases, a patient receiving the combination therapy disclosed herein can experience a Partial Response (PR), which roughly corresponds to at least a 50% decrease in the total tumor volume but with evidence of some residual disease still remaining. In some cases the residual disease in a deep partial response may actually be dead tumor or scar so that a few patients classified as having a PR may actually have a CR. Also many patients who show shrinkage during treatment show further shrinkage with continued treatment and may achieve a CR. In some cases, a patient receiving the combination therapy can experience a Minor Response (MR), which roughly means a small amount of shrinkage that is more than 25% of total tumor volume but less than the 50% that would make it a PR. In some cases, a patient receiving the combination therapy can exhibit Stable Disease (SD), which means the tumors stay roughly the same size, but can include either a small amount of growth (typically less than 20 or 25%) or a small amount of shrinkage (Anything less than a PR unless minor responses are broken out. If so, then SD is defined as typically less 25%).

Desired beneficial or desired clinical results from the combination therapy may also include e. g., reduced (i.e., slowing to some extent and/or stop) cancer cell infiltration into peripheral organs; inhibit (i.e., slow to some extent and/or stop) tumor metastasis; increased response rates (RR); increased duration of response; relieved to some extent one or more of the symptoms associated with the cancer; decreased dose of other medications required to treat the disease; delayed progression of the disease; and/or prolonged survival of patients and/or improved quality of life. Methods for evaluating these effects are well known and/or disclosed in, e.g., cancerguide.org/endpoints.html and RECIST guidelines, supra.

EXAMPLES

Example 1. HEPG2 Tyrosine Aminotransferase (TAT) Assay

The following protocol describes an assay for measuring induction of TAT by dexamethasone in HepG2 cells (a human liver hepatocellular carcinoma cell line; ECACC, UK). HepG2 cells are cultured using MEME media supplemented with 10% (v/v) foetal bovine serum; 2 mM L-glutamine and 1% (v/v) NEAA at 37° C., 5%/95% (v/v) $CO_2$/air. The HepG2 cells are then be counted and adjusted to yield a density of $0.125\times10^6$ cells/ml in RPMI 1640 without phenol red, 10% (v/v) charcoal stripped FBS, 2 mM L-glutamine and seeded at 25,000 cells/well in 200 µl into 96 well, sterile, tissue culture micro titre plates, and incubated at 37° C., 5% $CO_2$ for 24 hours.

Growth media are then removed and replaced with assay media {RPMI 1640 without phenol red, 2 mM L-glutamine+ 10 µM forskolin}. Test compounds are then be screened against a challenge of 100 nM dexamethasone. Compounds are then be serially half log diluted in 100% (v/v) dimethylsulfoxide from a 10 mM stock. Then an 8-point half-log dilution curve are generated followed by a 1:100 dilution into assay media to give a 10× final assay of the compound concentration, this results in final assay of the compound concentration that ranged 10 to 0.003 µM in 0.1% (v/v) dimethylsulfoxide.

Test compounds are pre-incubated with cells in microtitre plates for 30 minutes at 37° C., 5/95 (v/v) $CO_2$/air, before the addition of 100 nM dexamethasone and then subsequently for 20 hours to allow optimal TAT induction.

HepG2 cells are then lysed with 30 µl of cell lysis buffer containing a protease inhibitor cocktail for 15 minutes at 4° C. 155 µl of substrate mixture can then be added containing 5.4 mM Tyrosine sodium salt, 10.8 mM alpha ketoglutarate and 0.06 mM pyridoxal 5' phosphate in 0.1M potassium phosphate buffer (pH 7.4). After 2 hours incubation at 37° C. the reaction can be terminated by the addition of 15 µl of 10M aqueous potassium hydroxide solution, and the plates incubated for a further 30 minutes at 37° C. The TAT activity product can be measured by absorbance at λ 340 nm.

Half-maximal inhibition concentration ($IC_{50}$) values can be calculated by plotting % inhibition (normalised to 100 nM dexamethasone TAT stimulation) v. compound concentration and fitting the data to a 4 parameter logistic equation. $IC_{50}$ values can converted to Ki (equilibrium dissociation constant) using the Cheng and Prusoff equation, assuming the antagonists were competitive inhibitors with respect to dexamethasone.

Example 2. Inhibition of Glioblastoma Cell Growth with SGRM

The effect of GRMs on the growth in culture of human and mouse glioblastoma cells was examined. The GRMs mifepristone and CORT125134 inhibited growth in culture of each of five different glioblastoma cell lines. The highest drug concentration tested was 50 µM. The cell lines used were the Standard Serum Human glioblastoma (GBM) Cell lines: U251, GL261, U87, and the patient-derived neurosphere cell lines GBM8 and GBM4. Cells were plated at cell numbers of 2000 cells/well, in a 96-well format; the experiments were done in triplicate. Cell growth inhibition by the applied drugs was assayed. Cell growth inhibition was quantified by the Alamar Blue method using a commercial assay kit. Cell growth inhibition was determined ("read out") after 72 hours of treatment. The half-maximal inhibition concentration ($IC_{50}$) values determined for mifepristone ranged from about 16 micromolar (µM) to about 24 µM. The $IC_{50}$ values determined for CORT125134 ranged from about 5 µM to about 29 µM.

Cell Cultures:

The human glioblastoma cell lines (obtained from the American Type Culture Collection (ATCC), Manassas Va., USA) tested were U251 and U87 (human), and GL261 (mouse). These were grown as an adherent monolayer cultured in DMEM supplemented with 10% fetal bovine serum (FBS) (Seradigm, a subsidiary of VWR, Radnor Pa., USA) and 1% glutamine pen-strep (Omega Scientific, Tarzana Calif., USA). GBM8 (passage 12) and GBM4 are patient derived glioma stem cell lines obtained and cultured as neurospheres (spheroids) as described by Galli et al., "Isolation and characterization of tumorigenic, stem-like neural precursors from human glioblastoma" Cancer Res 2004, 64 (19), 7011-21 and Lee et al., "Tumor stem cells derived from glioblastomas cultured in bFGF and EGF more closely mirror the phenotype and genotype of primary tumors than do serum-cultured cell lines" Cancer Cell 2006, 9 (5), 391-403. Initial GBM surgical samples were dissociated in stem cell isolation medium containing human recombinant EGF (20 ng/µl), human bFGF (10 ng/µl) and heparin (2 µg/ml), washed, filtered through a 30 µm mesh and plated onto ultra-low adherence flasks at a concentration of $5×10^5$ to $1.5×10^6$ viable cells/ml. Sphere cultures were passaged by dissociation, washing and resuspension in neural stem cell culture medium (NeuroCult™ NS-A Proliferation kit #05751, Stemcell Technologies, Vancouver, BC, CA), according to the manufacturer's instructions.

Cell Viability Assay:

Cells were seeded into 96-well plates at a density of 2000 cells per well. Compounds were added 24 hours after the seeding of cells. All compounds were diluted in 1% FBS/DMEM. The control was treated with media alone. After 3 days incubation (37° C./5% $CO_2$) Alamar Blue (#BUF012B, AbDSerotec, Kidlington, UK) was added according to the manufacturer's protocol, directly to the medium and placed back in the tissue culture incubator (37° C. 5% $CO_2$). After 3-18 hours fluorescent signal was read at 544 ex/590 cm (SpectraMax i3x plate reader, Molecular Devices, San Jose Calif., USA) to determine the number of viable cells. The $IC_{50}$ values were calculated using commercial software (Prism 5 Software, GraphPad, La Jolla Calif., USA).

After 24 hours post incubation, cells were treated with drugs at various concentrations for 72 hours. Cell viability was measured after 72 hours by Alamar Blue and results reported as triplicate experiment. The following Table presents the $IC_{50}$ values as determined in these experiments.

TABLE

Effects of Mifepristone and CORT 125134 on Standard GBM and Neurosphere GBM lines
Cell Growth Inhibition ($IC_{50}$ µM)

| Compound | Cell Line | | | | |
|---|---|---|---|---|---|
| | GL261 | U87 | U251 | GBM4 | GBM8 |
| Mifepristone | 15.74 | 18.4 | 18.4 | 24.10 | 23.96 |
| CORT125134 | 5.86 | 5.42 | 12.5 | 20.68 | 29.07 |

Example 3. Treating a Meningioma Patient with SGRM

A 52-year-old female patient complains of tinnitus and right-sided hearing loss for 6 months. The enhanced axial T1-weighted MRI of the posterior fossa shows a 16-×11-×18 mm large, heterogeneous, sessile lesion, which extends into her internal auditory canal. She is treated with CORT125134 at a dose of 200 mg once a day for eight weeks. Her tumor load is monitored using enhanced MRI before, during and after the treatment. The imaging results indicate that the size of the tumor is decreased as compared to the tumor size before treatment baseline, and the reduction is more than 50% at the end of the treatment period.

Example 4. Treating a Meningioma Patient with SGRM

A 52-year-old female patient complains of tinnitus and right-sided hearing loss for 6 months. The enhanced axial T1-weighted MRI of the posterior fossa shows a 16-×11-×18 mm large, heterogeneous, sessile lesion, which extends into her internal auditory canal. She is treated with CORT125281 at a dose of 200 mg once a day for eight weeks. Her tumor load is monitored using enhanced MRI before, during and after the treatment. The imaging results indicate that the size of the tumor is decreased as compared to baseline, and the reduction is more than 50% at the end of the treatment period.

All patents, patent publications, and all other publications cited herein are hereby incorporated by reference herein in their entireties for all purposes.

What is claimed is:

1. A method of treating a GR+ meningioma in a subject, the method comprising administering to the subject a nonsteroidal selective glucocorticoid receptor antagonist (SGRA) in an amount effective to reduce the tumor load of the meningioma in the patient with the proviso that the subject not be otherwise suffering from a disorder treatable with a SGRA, nor does the meningioma secrete adrenocorticotropic hormone (ACTH).

2. The method of claim 1, wherein the method comprises administering the nonsteroidal SGRA for at least two weeks.

3. The method of claim 1, wherein the effective amount is a daily dose of between 1 and 100 mg/kg/day, wherein the nonsteroidal SGRA is administered alone or with at least one non-SGRA therapy, wherein the at least one non-SGRA therapy is a chemotherapy, a radiation therapy or other therapeutic agents.

4. The method of claim 3, wherein the daily dose is 1, 2, 4, 6, 8, 10, 12, 14, 16, 18, 20, 30, 40, 50 60, 70, 80, 90 or 100 mg/kg/day.

5. The method of claim 1, wherein the nonsteroidal SGRA is administrated for at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, or 80 weeks.

6. The method of claim 1, wherein the nonsteroidal SGRA is a cyclohexyl pyrimidine.

7. The method of claim 6, wherein the cyclohexyl pyrimidine has the following formula:

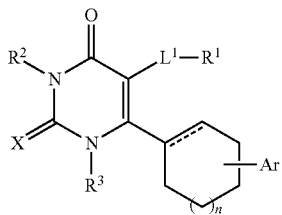

wherein
the dashed line is absent or a bond;
X is selected from the group consisting of O and S;
$R^1$ is selected from the group consisting of cycloalkyl, heterocycloalkyl, aryl and heteroaryl, optionally substituted with from 1 to 3 $R^{1a}$ groups;
each $R^{1a}$ is independently selected from the group consisting of H, $C_{1-6}$ alkyl, $C_{2-6}$ alkenyl, $C_{2-6}$ alkynyl, $C_{1-6}$ alkoxy, $C_{1-6}$ alkyl $OR^{1b}$, halogen, $C_{1-6}$ haloalkyl, $C_{1-6}$ haloaloxy, $OR^{1b}$, $NR^{1b}R^{1c}$, $C(O)R^{1b}$, $C(O)OR^{1b}$, $OC(O)R^{1b}$, $C(O)NR^{1b}R^{1c}$, $NR^{1b}C(O)R^{1c}$, $SO_2R^{1b}$, $SO_2NR^{1b}R^{1c}$, cycloalkyl, heterocycloalkyl, aryl and heteroaryl;
$R^{1b}$ and $R^{1c}$ are each independently selected from the group consisting of H and $C_{1-6}$ alkyl;
$R^2$ is selected from the group consisting of H, $C_{1-6}$ alkyl, $C_{1-6}$ alkyl-$OR^{1b}$, $C_{1-6}$ alkyl $NR^{1b}R^{1c}$ and $C_{1-6}$ alkylene heterocycloalkyl;
$R^3$ is selected from the group consisting of H and $C_{1-6}$ alkyl;

Ar is aryl, optionally substituted with 1-4 $R^4$ groups;
each $R^4$ is independently selected from the group consisting of H, $C_{1-6}$ alkyl, $C_{1-6}$ alkoxy, halogen, $C_{1-6}$ haloalkyl and $C_{1-6}$ haloalkoxy;
$L^1$ is a bond or $C_{1-6}$ alkylene; and
subscript n is an integer from 0 to 3,
or salts and isomers thereof.

8. The method of claim 6, wherein the cyclohexyl pyrimidine has the following formula:

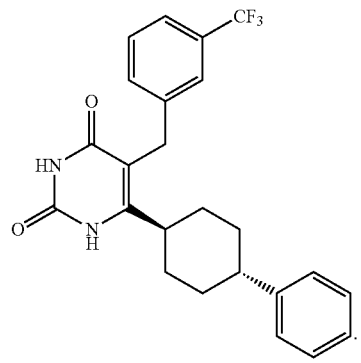 [SMILES: O=c1[nH]c(=O)c(Cc2cccc(C(F)(F)F)c2)c([C@H]2CC[C@H](c3ccccc3)CC2)[nH]1]

9. The method of claim 1, wherein the nonsteroidal SGRA is a fused azadecalin.

10. The method of claim 9, wherein the fused azadecalin is a compound having the following formula:

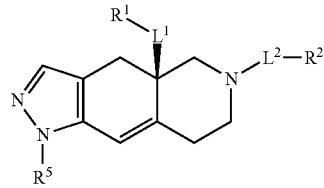

wherein
$L^1$ and $L^2$ are members independently selected from a bond and unsubstituted alkylene;
$R^1$ is a member selected from unsubstituted alkyl, unsubstituted heteroalkyl, unsubstituted heterocycloalkyl, —$OR^{1A}$, $NR^{1C}R^{1D}$, —$C(O)NR^{1C}R^{1D}$, and —$C(O)OR^{1A}$, wherein
$R^{1A}$ is a member selected from hydrogen, unsubstituted alkyl and unsubstituted heteroalkyl,
$R^{1C}$ and $R^{1D}$ are members independently selected from unsubstituted alkyl and unsubstituted heteroalkyl, wherein $R^{1C}$ and $R^{1D}$ are optionally joined to form an unsubstituted ring with the nitrogen to which they are attached, wherein said ring optionally comprises an additional ring nitrogen;
$R^2$ has the formula:

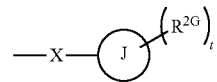

wherein
$R^{2G}$ is a member selected from hydrogen, halogen, unsubstituted alkyl, unsubstituted heteroalkyl, unsubstituted cycloalkyl, unsubstituted heterocycloalkyl, —CN, and —CF$_3$;

J is phenyl;

t is an integer from 0 to 5;

X is —S(O$_2$)—; and

R$^5$ is phenyl optionally substituted with 1-5 R$^{5A}$ groups, wherein

R$^{5A}$ is a member selected from hydrogen, halogen, —OR$^{5A1}$, S(O$_2$)NR$^{5A2}$R$^{5A3}$, —CN, and unsubstituted alkyl, wherein R$^{5A1}$ is a member selected from hydrogen and unsubstituted alkyl, and R$^{5A2}$ and R$^{5A3}$ are members independently selected from hydrogen and unsubstituted alkyl, or salts and isomers thereof.

11. The method of claim 9, wherein the fused azadecalin is:

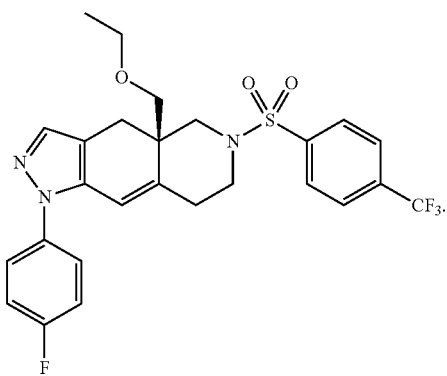

12. The method of claim 1, wherein the nonsteroidal SGRA is a heteroaryl ketone fused azadecalin or an octahydro fused azadecalin.

13. The method of claim 12, wherein the heteroaryl ketone fused azadecalin has the formula:

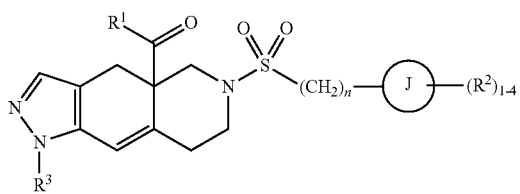

wherein

R$^1$ is a heteroaryl ring having from 5 to 6 ring members and from 1 to 4 heteroatoms each independently selected from the group consisting of N, O and S, optionally substituted with 1-4 groups each independently selected from R$^{1a}$;

each R$^{1a}$ is independently selected from the group consisting of hydrogen, C$_{1-6}$ alkyl, halogen, C$_{1-6}$ haloalkyl, C$_{1-6}$ alkoxy, C$_{1-6}$ haloalkoxy, CN, N-oxide, C$_{3-8}$ cycloalkyl, and C$_{3-8}$ heterocycloalkyl;

ring J is selected from the group consisting of a cycloalkyl ring, a heterocycloalkyl ring, an aryl ring and a heteroaryl ring, wherein the heterocycloalkyl and heteroaryl rings have from 5 to 6 ring members and from 1 to 4 heteroatoms each independently selected from the group consisting of N, O and S;

each R$^2$ is independently selected from the group consisting of hydrogen, C$_{1-6}$ alkyl, halogen, C$_{1-6}$ haloalkyl, C$_{1-6}$ alkoxy, C$_{1-6}$ haloalkoxy, C$_{1-6}$ alkyl-C$_{1-6}$ alkoxy, CN, OH, NR$^{2a}$R$^{2b}$, C(O)R$^{2a}$, C(O)OR$^{2a}$, C(O)NR$^{2a}$R$^{2b}$, SR$^{2a}$, S(O)R$^{2a}$, S(O)$_2$R$^{2a}$, C$_{3-8}$ cycloalkyl, and C$_{3-8}$ heterocycloalkyl, wherein the heterocycloalkyl groups are optionally substituted with 1-4 R$^{2c}$ groups;

alternatively, two R$^2$ groups linked to the same carbon are combined to form an oxo group (=O);

alternatively, two R$^2$ groups are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 R$^{2d}$ groups;

R$^{2a}$ and R$^{2b}$ are each independently selected from the group consisting of hydrogen and C$_{1-6}$ alkyl;

each R$^{2c}$ is independently selected from the group consisting of hydrogen, halogen, hydroxy, C$_{1-6}$ alkoxy, C$_{1-6}$ haloalkoxy, CN, and NR$^{2a}$R$^{2b}$;

each R$^{2d}$ is independently selected from the group consisting of hydrogen and C$_{1-6}$ alkyl, or two R$^{2d}$ groups attached to the same ring atom are combined to form (=O);

R$^3$ is selected from the group consisting of phenyl and pyridyl, each optionally substituted with 1-4 R$^{3a}$ groups;

each R$^{3a}$ is independently selected from the group consisting of hydrogen, halogen, and C$_{1-6}$ haloalkyl; and subscript n is an integer from 0 to 3;

or salts and isomers thereof.

14. The method of claim 12, wherein the heteroarylketone fused azadecalin is selected from the group consisting of:

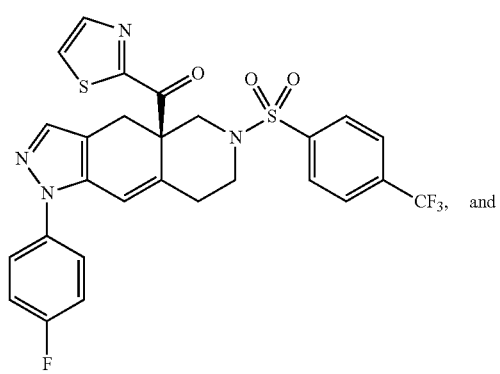

and

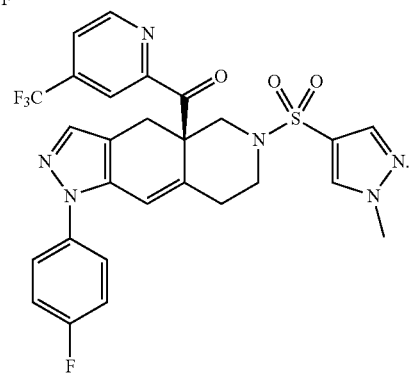

15. The method of claim 12, wherein the octahydro fused azadecalin has the formula:

[Chemical structure]

wherein
$R^1$ is a heteroaryl ring having from 5 to 6 ring members and from 1 to 4 heteroatoms each independently selected from the group consisting of N, O and S, optionally substituted with 1-4 groups each independently selected from $R^{1a}$;
each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, N-oxide, and $C_{3-8}$ cycloalkyl;
ring J is selected from the group consisting of an aryl ring and a heteroaryl ring having from 5 to 6 ring members and from 1 to 4 heteroatoms each independently selected from the group consisting of N, O and S;
each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, CN, OH, $NR^{2a}R^{2b}$, $C(O)R^{2a}$, $C(O)OR^{2a}$, $C(O)NR^{2a}R^{2b}$, $SR^{2a}$, $S(O)R^{2a}$, $S(O)_2R^{2a}$, $C_{3-8}$ cycloalkyl, and $C_{3-8}$ heterocycloalkyl having from 1 to 3 heteroatoms each independently selected from the group consisting of N, O and S;
alternatively, two $R^2$ groups on adjacent ring atoms are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2c}$ groups;
$R^{2a}$, $R^{2b}$ and $R^{2c}$ are each independently selected from the group consisting of hydrogen and $C_{1-6}$ alkyl;
each $R^{3a}$ is independently halogen; and
subscript n is an integer from 0 to 3,
or salts and isomers thereof.

16. The method of claim 12, wherein the octahydro fused azadecalin has the formula:

[Chemical structure]

17. The method of claim 1, wherein the nonsteroidal SGRA is CORT125134 or CORT125281.

18. A method of treating a meningioma in a patient, the method comprising administering to the subject a nonsteroidal selective glucocorticoid receptor antagonist (SGRA) in an amount effective to reduce the tumor load of meningioma in the patient.

19. The method of claim 18, wherein the method comprises administering the nonsteroidal SGRA for at least two weeks.

20. The method of claim 18, wherein the effective amount is a daily dose of between 1 and 100 mg/kg/day.

21. The method of claim 20, wherein the daily dose is 1, 2, 4, 6, 8, 10, 12, 14, 16, 18, 20, 30, 40, 50 60, 70, 80, 90 or 100 mg/kg/day.

22. The method of claim 18, wherein the nonsteroidal SGRA is administrated for at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, or 80 weeks.

23. The method of claim 18, wherein the nonsteroidal SGRA is a cyclohexyl pyrimidine.

24. The method of claim 23, wherein the cyclohexyl pyrimidine has the following formula:

[Chemical structure]

wherein
the dashed line is absent or a bond;
X is selected from the group consisting of O and S;
$R^1$ is selected from the group consisting of cycloalkyl, heterocycloalkyl, aryl and heteroaryl, optionally substituted with from 1 to 3 $R^{1a}$ groups;
each $R^{1a}$ is independently selected from the group consisting of H, $C_{1-6}$ alkyl, $C_{2-6}$ alkenyl, $C_{2-6}$ alkynyl, $C_{1-6}$ alkoxy, $C_{1-6}$ alkyl $OR^{1b}$, halogen, $C_{1-6}$ haloalkyl, $C_{1-6}$ haloaloxy, $OR^{1b}$, $NR^{1b}R^{1c}$, $C(O)R^{1b}$, $C(O)OR^{1b}$, $OC(O)R^{1b}$, $C(O)NR^{1b}R^{1c}$, $NR^{1b}C(O)R^{1c}$, $SO_2R^{1b}$, $SO_2NR^{1b}R^{1c}$, cycloalkyl, heterocycloalkyl, aryl and heteroaryl;
$R^{1b}$ and $R^{1c}$ are each independently selected from the group consisting of H and $C_{1-6}$ alkyl;
$R^2$ is selected from the group consisting of H, $C_{1-6}$ alkyl, $C_{1-6}$ alkyl-$OR^{1b}$, $C_{1-6}$ alkyl $NR^{1b}R^{1c}$ and $C_{1-6}$ alkylene heterocycloalkyl;
$R^3$ is selected from the group consisting of H and $C_{1-6}$ alkyl;
Ar is aryl, optionally substituted with 1-4 $R^4$ groups;
each $R^4$ is independently selected from the group consisting of H, $C_{1-6}$ alkyl, $C_{1-6}$ alkoxy, halogen, $C_{1-6}$ haloalkyl and $C_{1-6}$ haloalkoxy;
$L^1$ is a bond or $C_{1-6}$ alkylene; and
subscript n is an integer from 0 to 3,
or salts and isomers thereof.

25. The method of claim 23, wherein the cyclohexyl pyrimidine has the following formula:

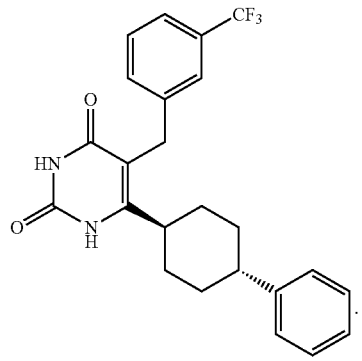

26. The method of claim 18, wherein the nonsteroidal SGRA is a fused azadecalin.

27. The method of claim 26, wherein the fused azadecalin is a compound having the following formula:

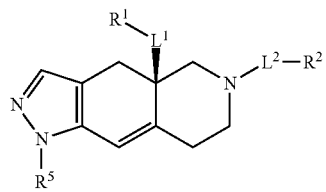

wherein
- $L^1$ and $L^2$ are members independently selected from a bond and unsubstituted alkylene;
- $R^1$ is a member selected from unsubstituted alkyl, unsubstituted heteroalkyl, unsubstituted heterocycloalkyl, —$OR^{1A}$, $NR^{1C}R^{1D}$, —$C(O)NR^{1C}R^{1D}$, and —$C(O)OR^{1A}$, wherein
  - $R^{1A}$ is a member selected from hydrogen, unsubstituted alkyl and unsubstituted heteroalkyl,
  - $R^{1C}$ and $R^{1D}$ are members independently selected from unsubstituted alkyl and unsubstituted heteroalkyl, wherein $R^{1C}$ and $R^{1D}$ are optionally joined to form an unsubstituted ring with the nitrogen to which they are attached, wherein said ring optionally comprises an additional ring nitrogen;
- $R^2$ has the formula:

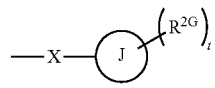

wherein
- $R^{2G}$ is a member selected from hydrogen, halogen, unsubstituted alkyl, unsubstituted heteroalkyl, unsubstituted cycloalkyl, unsubstituted heterocycloalkyl, —CN, and —$CF_3$;
- J is phenyl;
- t is an integer from 0 to 5;
- X is —$S(O_2)$—; and
- $R^5$ is phenyl optionally substituted with 1-5 $R^{5A}$ groups, wherein $R^{5A}$ is a member selected from hydrogen, halogen, —$OR^{5A1}$, $S(O_2)NR^{5A2}R^{5A3}$, —CN, and unsubstituted alkyl, wherein
- $R^{5A1}$ is a member selected from hydrogen and unsubstituted alkyl, and
- $R^{5A2}$ and $R^{5A3}$ are members independently selected from hydrogen and unsubstituted alkyl, or salts and isomers thereof.

28. The method of claim 26, wherein the fused azadecalin is:

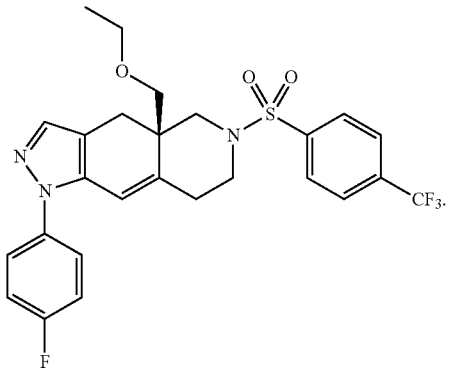 [SMILES: CCOC[C@]12Cc3cnn(-c4ccc(F)cc4)c3C=C1CCN(S(=O)(=O)c1ccc(C(F)(F)F)cc1)C2]

29. The method of claim 18, wherein the nonsteroidal SGRA is a heteroaryl ketone fused azadecalin or an octahydro fused azadecalin.

30. The method of claim 29, wherein the heteroaryl ketone fused azadecalin has the formula:

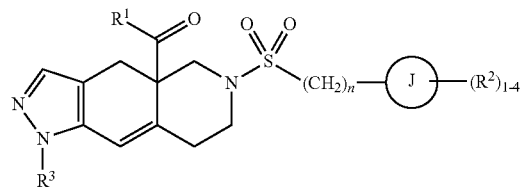

wherein
- $R^1$ is a heteroaryl ring having from 5 to 6 ring members and from 1 to 4 heteroatoms each independently selected from the group consisting of N, O and S, optionally substituted with 1-4 groups each independently selected from $R^{1a}$;
- each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, CN, N-oxide, $C_{3-8}$ cycloalkyl, and $C_{3-8}$ heterocycloalkyl;
- ring J is selected from the group consisting of a cycloalkyl ring, a heterocycloalkyl ring, an aryl ring and a heteroaryl ring, wherein the heterocycloalkyl and heteroaryl rings have from 5 to 6 ring members and from 1 to 4 heteroatoms each independently selected from the group consisting of N, O and S;
- each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, CN, OH, $NR^{2a}R^{2b}$, $C(O)R^{2a}$, $C(O)OR^{2a}$, $C(O)NR^{2a}R^{2b}$, $SR^{2a}$, $S(O)R^{2a}$, $S(O)_2R^{2a}$, $C_{3-8}$ cycloalkyl, and $C_{3-8}$ heterocycloalkyl, wherein the heterocycloalkyl groups are optionally substituted with 1-4 $R^{2c}$ groups;

alternatively, two R² groups linked to the same carbon are combined to form an oxo group (=O);

alternatively, two R² groups are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2d}$ groups;

$R^{2a}$ and $R^{2b}$ are each independently selected from the group consisting of hydrogen and $C_{1-6}$ alkyl;

each $R^{2c}$ is independently selected from the group consisting of hydrogen, halogen, hydroxy, $C_{1-6}$ alkoxy, $C_{1-6}$ haloalkoxy, CN, and $NR^{2a}R^{2b}$;

each $R^{2d}$ is independently selected from the group consisting of hydrogen and $C_{1-6}$ alkyl, or two $R^{2d}$ groups attached to the same ring atom are combined to form (=O);

$R^3$ is selected from the group consisting of phenyl and pyridyl, each optionally substituted with 1-4 $R^{3a}$ groups;

each $R^{3a}$ is independently selected from the group consisting of hydrogen, halogen, and $C_{1-6}$ haloalkyl; and subscript n is an integer from 0 to 3;

or salts and isomers thereof.

31. The method of claim 29, wherein the heteroarylketone fused azadecalin is selected from the group consisting of:

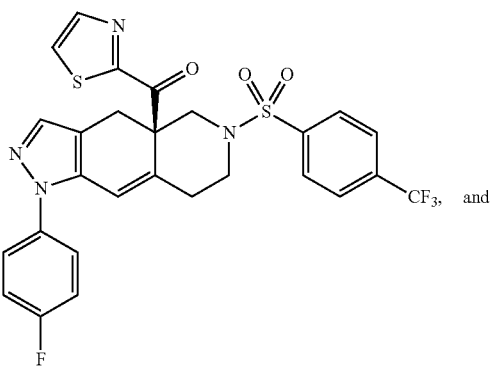

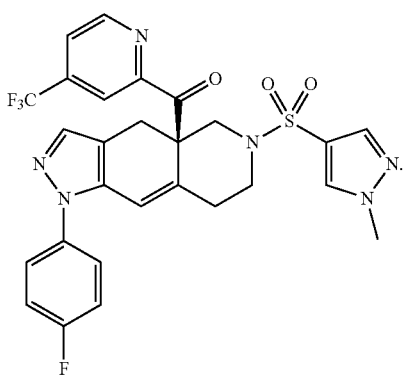

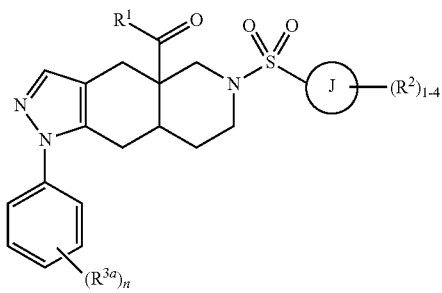

wherein $R^1$ is a heteroaryl ring having from 5 to 6 ring members and from 1 to 4 heteroatoms each independently selected from the group consisting of N, O and S, optionally substituted with 1-4 groups each independently selected from $R^{1a}$;

each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, N-oxide, and $C_{3-8}$ cycloalkyl;

ring J is selected from the group consisting of an aryl ring and a heteroaryl ring having from 5 to 6 ring members and from 1 to 4 heteroatoms each independently selected from the group consisting of N, O and S;

each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, CN, OH, $NR^{2a}R^{2b}$, $C(O)R^{2a}$, $C(O)OR^{2a}$, $C(O)NR^{2a}R^{2b}$, $SR^{2a}$, $S(O)R^{2a}$, $S(O)_2R^{2a}$, $C_{3-8}$ cycloalkyl, and $C_{3-8}$ heterocycloalkyl having from 1 to 3 heteroatoms each independently selected from the group consisting of N, O and S;

alternatively, two R² groups on adjacent ring atoms are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2c}$ groups;

$R^{2a}$, $R^{2b}$ and $R^{2c}$ are each independently selected from the group consisting of hydrogen and $C_{1-6}$ alkyl;

each $R^{3a}$ is independently halogen; and subscript n is an integer from 0 to 3, or salts and isomers thereof.

33. The method of claim 29, wherein the octahydro fused azadecalin has the formula:

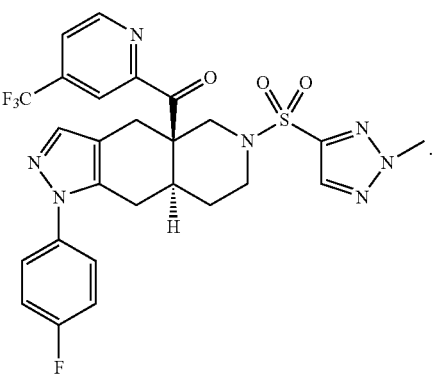 [SMILES: Cn1ncc(S(=O)(=O)N2CC[C@H]3Cc4c(cnn4-c4ccc(F)cc4)C[C@]3(C(=O)c3cc(C(F)(F)F)ccn3)C2)n1]

32. The method of claim 29, wherein the octahydro fused azadecalin has the formula:

34. The method of claim 18, wherein the nonsteroidal SGRA is CORT125134 or CORT125281.

\* \* \* \* \*